US008034900B2

(12) United States Patent
Miranda et al.

(10) Patent No.: US 8,034,900 B2

(45) Date of Patent: Oct. 11, 2011

(54) WATER-SOLUBLE THIOESTER AND SELENOESTER COMPOUNDS AND METHODS FOR MAKING AND USING THE SAME

(75) Inventors: Leslie Philip Miranda, San Francisco, CA (US); Stephen B. H. Kent, San Francisco, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 687 days.

(21) Appl. No.: 10/541,078

(22) PCT Filed: Dec. 30, 2003

(86) PCT No.: PCT/US03/41542

§ 371 (c)(1),
(2), (4) Date: Feb. 7, 2006

(87) PCT Pub. No.: WO2004/061094

PCT Pub. Date: Jul. 22, 2004

(65) Prior Publication Data

US 2006/0173159 A1 Aug. 3, 2006

Related U.S. Application Data

(60) Provisional application No. 60/437,285, filed on Dec. 30, 2002.

(51) Int. Cl.
*A61K 38/00* (2006.01)

(52) U.S. Cl. ...................................................... 530/333

(58) Field of Classification Search ........................ None
See application file for complete search history.

(56) References Cited

U.S. PATENT DOCUMENTS

| | | | |
|---|---|---|---|
| 4,179,337 | A | 12/1979 | Davis et al. |
| 5,075,046 | A | 12/1991 | Stoll |
| 5,089,261 | A | 2/1992 | Nitecki et al. |
| 5,100,992 | A | 3/1992 | Cohn et al. |
| 5,134,192 | A | 7/1992 | Feijen et al. |
| 5,166,309 | A | 11/1992 | Maj et al. |
| 5,171,264 | A | 12/1992 | Merrill |
| 5,213,891 | A | 5/1993 | Maj et al. |
| 5,219,564 | A | 6/1993 | Zalipsky et al. |
| 5,275,838 | A | 1/1994 | Merrill |
| 5,281,698 | A | 1/1994 | Nitecki |
| 5,298,643 | A | 3/1994 | Greenwald |
| 5,312,808 | A | 5/1994 | Shorr |
| 5,321,095 | A | 6/1994 | Greenwald |
| 5,324,844 | A | 6/1994 | Zalipsky |
| 5,349,001 | A | 9/1994 | Greenwald et al. |
| 5,352,756 | A | 10/1994 | Meldal |
| 5,446,090 | A | 8/1995 | Harris |
| 5,455,027 | A | 10/1995 | Zalipsky et al. |
| 5,470,829 | A | 11/1995 | Prisell et al. |
| 5,478,805 | A | 12/1995 | Shorr |
| 5,567,422 | A | 10/1996 | Greenwald |
| 5,605,976 | A | 2/1997 | Martinez |
| 5,612,460 | A | 3/1997 | Zalipsky |
| 5,614,549 | A | 3/1997 | Greenwald et al. |
| 5,618,528 | A | 4/1997 | Cooper et al. |
| 5,637,749 | A | 6/1997 | Greenwald |
| 5,643,575 | A | 7/1997 | Martinez et al. |
| 5,650,388 | A | 7/1997 | Shorr et al. |
| 5,672,662 | A | 9/1997 | Harris et al. |
| 5,681,567 | A | 10/1997 | Martinez et al. |
| 5,686,110 | A | 11/1997 | Greenwald et al. |
| 5,730,990 | A | 3/1998 | Greenwald et al. |
| 5,739,208 | A | 4/1998 | Harris |
| 5,756,593 | A | 5/1998 | Martinez et al. |
| 5,808,096 | A | 9/1998 | Zalipsky |
| 5,824,778 | A | 10/1998 | Ishikawa et al. |
| 5,824,784 | A | 10/1998 | Kinstler et al. |
| 5,840,900 | A | 11/1998 | Greenwald et al. |
| 5,863,984 | A | 1/1999 | Doillon et al. |
| 5,874,500 | A | 2/1999 | Rhee et al. |
| 5,880,131 | A | 3/1999 | Greenwald et al. |
| 5,900,461 | A | 5/1999 | Harris |
| 5,902,588 | A | 5/1999 | Greenwald et al. |
| 5,919,422 | A | 7/1999 | Yamanaka et al. |
| 5,919,455 | A | 7/1999 | Greenwald et al. |
| 5,932,462 | A | 8/1999 | Harris et al. |

(Continued)

FOREIGN PATENT DOCUMENTS

WO WO 90/13540 11/1990

(Continued)

OTHER PUBLICATIONS

Sasaki & Koga, "Biomimetic studies using artificial systems. IV. Biomimetic peptide synthesis by using multifunctionalized crown ethers as a novel enzyme model. A new concept in mimicking of enzyme-catalyzed bond-forming reactions." Chem. Pharm. Bull., 1989, 37, 912-9.*

Sasaki & Koga "Multi-functionalized chiral crown ethers as enzyme models for the synthesis of peptides. Multiple chiral recognition in the enzyme model ," J. Inclus. Phen. Mol. Recog. Chem., 1989, 7, 267-76.*

Baca et al. "Chemical Ligation of Cysteine-Containing Peptides: Synthesis of a 22 kDa Tethered Dimer of HIV-1 Protease," J. Am. Chem. Soc., 1995, 117, 1881-7.*

Dawson et al., "Synthesis of Proteins by Native Chemical Ligation", Science (1994) 266:776-779.

Hackeng et al., "Protein Synthesis by Native Chemical Ligation: Expanded Scope by Using Straightforward Methodology", PNAS (1999) 96: 10068-10073.

Schnolzer et al., "In situ neutralization in Boc-chemistry solid phase peptide synthesis", Int. J. Pept. Prot. Res., (1992) 40:180-193.

(Continued)

*Primary Examiner* — Cecilia J Tsang
*Assistant Examiner* — Thomas Heard

(57) ABSTRACT

Water-soluble thioester and selenoester compounds, their generators, as well as methods for making and using the same, are provided. The subject thioester and selenoester compounds are characterized by including an amino acid synthon having a C-terminal group bonded to a water-soluble polymer through a thioester or selenoester linkage. Solid phase resins and protocols for generating the subject compounds are also provided. The subject water soluble thioester and selenoester compounds and generators find use in a variety of different applications, including thioester or selenoester mediated chemical ligation reactions.

15 Claims, 3 Drawing Sheets

U.S. PATENT DOCUMENTS

| | | | |
|---|---|---|---|
| 5,965,119 | A | 10/1999 | Greenwald et al. |
| 5,965,566 | A | 10/1999 | Greenwald et al. |
| 5,985,263 | A | 11/1999 | Lee et al. |
| 5,990,237 | A | 11/1999 | Bentley et al. |
| 6,011,042 | A | 1/2000 | Greenwald et al. |
| 6,013,283 | A | 1/2000 | Greenwald et al. |
| 6,077,939 | A | 6/2000 | Wei et al. |
| 6,113,906 | A | 9/2000 | Greenwald et al. |
| 6,127,355 | A | 10/2000 | Greenwald et al. |
| 6,177,087 | B1 | 1/2001 | Greenwald et al. |
| 6,180,095 | B1 | 1/2001 | Greenwald et al. |
| 6,184,344 | B1 | 2/2001 | Kent et al. |
| 6,194,580 | B1 | 2/2001 | Greenwald et al. |
| 6,214,966 | B1 | 4/2001 | Harris |
| 6,307,018 | B1 | 10/2001 | Kent et al. |
| 6,326,468 | B1 | 12/2001 | Canne et al. |
| 6,340,742 | B1 | 1/2002 | Burg et al. |
| 2003/0149234 | A1 | 8/2003 | Botti et al. |

FOREIGN PATENT DOCUMENTS

| | | |
|---|---|---|
| WO | WO 92/00748 | 1/1992 |
| WO | WO 92/16555 | 10/1992 |
| WO | WO 94/04193 | 3/1994 |
| WO | WO 94/14758 | 7/1994 |
| WO | WO 94/17039 | 8/1994 |
| WO | WO 94/18247 | 8/1994 |
| WO | WO 94/28937 | 12/1994 |
| WO | WO 95/11924 | 5/1995 |
| WO | WO 95/13312 | 5/1995 |
| WO | WO 96/00080 | 1/1996 |
| WO | WO 96/21469 | 7/1996 |
| WO | WO 96/23794 | 8/1996 |
| WO | WO 96/34878 | 11/1996 |
| WO | WO 97/03106 | 1/1997 |
| WO | WO 98/07713 | 2/1998 |
| WO | WO 98/28434 | 7/1998 |
| WO | WO 98/41562 | 9/1998 |
| WO | WO 98/48837 | 11/1998 |
| WO | WO 98/56807 | 12/1998 |
| WO | WO 99/33483 | 12/1998 |
| WO | WO 99/30727 | 6/1999 |
| WO | WO 99/32134 | 7/1999 |
| WO | WO 99/45964 | 9/1999 |
| WO | WO 99/53951 | 10/1999 |
| WO | WO 00/12587 | 3/2000 |
| WO | WO 01/26692 | 4/2001 |
| WO | WO 02/18417 | 3/2002 |
| WO | WO 02/19963 | 3/2002 |
| WO | WO 02/20033 | 3/2002 |
| WO | WO 02/20557 | 3/2002 |

OTHER PUBLICATIONS

Schnolzer et al., "Constructing Proteins by Dovetailing Unprotected Synthetic Peptides: Backbone-Engineered HIV Protease", Science (1992) 256:221-225.

Englebretsen et al., "A Novel Thioether Linker: Chemical Synthesis of a HIV-1 Protease Analogue by Thioether Ligation", Tet. Letts. (1995) 36(48):8871-8874.

Yan et al., "Synthesis of Peptides and Proteins without Cysteine Residues by Native Chemical Ligation Combined with Desulfurization," J. Am. Chem. Soc. (2001) 123:526-533.

Gieselman et al., "Synthesis of a Selenocysteine-Containing Peptide by Native Chemical Ligation", Org. Lett. (2001) 3(9):1331-1334.

Canne et al., "A General Method for the Synthesis of Thioester Resin Linkers for Use in the Solid Phase Synthesis of Peptide-α-Thioacids", Tetrahedron Lett. (1995) 36(8):1217-1220.

Ingenito et al., "Solid Phase Synthesis of Peptide C-Terminal Thioesters by Fmoc/*t*-Bu Chemistry", J. Am. Chem. Soc. (1999) 121(49):11369-11374.

Dawson, et al., "Synthesis of Native Proteins by Chemical Ligation", Annual Review of Biochemistry, (2000) 69:923-960.

Schnolzer, et al., "Constructing Proteins by Dovetailing Unprotected Synthetic Peptides: Backbone-Engineered HIV Protease", Science, American Association for the Advancement of Science (1992) 256:221-225.

* cited by examiner (1A)

(1B)

(1C)

(1D)

WATER-SOLUBLE THIOESTER AND SELENOESTER COMPOUNDS AND METHODS FOR MAKING AND USING THE SAME

CROSS-REFERENCE TO RELATED APPLICATIONS

This application claims the benefit of U.S. Provisional Application Ser. No. 60/437,285, filed Dec. 30, 2002, which application is incorporated herein by reference in its entirety.

INTRODUCTION

1. Field of the Invention

The invention relates to thioester and selenoester compounds, their manufacture and use, and more particularly peptide thioesters and peptide selenoesters, their generators, synthesis, and use.

2. Background of the Invention

Thioesters and selenoesters represent an important class of molecules that readily react with nucleophiles. Thioesters are particularly useful for conjugation and chemoselective ligation reactions. Chemical ligation involves the chemoselective covalent linkage of a first chemical component to a second chemical component. Unique, mutually reactive functional groups present on the first and second components can be used to render the ligation reaction chemoselective. For example, thioesters are commonly used to direct the chemoselective chemical ligation of peptides and polypeptides. Several different thioester-mediated chemistries have been utilized for this purpose, such as native chemical ligation (Dawson, et al., *Science* (1994) 266:776-779; Kent, et al., WO 96/34878; Kent, et al., WO 98/28434), and involve the use of peptide thioesters and peptide selenoesters.

Synthesis of peptide thioesters and selenoesters is typically carried out using the principals of solid phase organic chemistry (Hackeng, et al., PNAS (1999) 96: 10068-10073; and Schnolzer, et al., Int. J. Pept. Prot. Res., (1992) 40:180-193). Solid phase peptide synthesis (SPPS) involves the stepwise assembly of amino acids on a solid support. Peptides are "grown" on the support through successive cycles of coupling and deprotection of incoming amino acids, followed by cleavage of the assembled peptide from the support. The initial cleavage product is considered to be "crude" as it contains the desired peptide along with partial sequences, side reactants, residual organics and the like. So subsequent purification of the desired product from the crude cleavage product is typically required. Unfortunately, some peptide sequences can be difficult to make and purify.

Solubility is one factor that influences the synthesis and subsequent handling properties of the peptide. In addition, even though on-resin chain assembly and cleavage may proceed efficiently, the crude cleavage product of a "difficult" peptide once released from the support can be poorly soluble in aqueous or mixed aqueous-organic solutions and may form aggregates. Such peptides appear as a smear of products when the crude product is examined by various analytical techniques such as High Performance Liquid Chromatography (HPLC). Thus, the desired product can be difficult to separate from the crude cleavage product, resulting in lower purity and lower overall purification yields.

Synthesis of difficult peptide thioesters and selenoesters represents additional challenges since care must be taken to avoid nucleophiles during synthesis, purification and during handling of the peptides. Moreover, for those peptide thioesters and selenoesters that exhibit poor handling properties, such as low solubility or aggregation in aqueous solution, the rate, purity and overall yield of a given peptide ligation reaction can be diminished.

Accordingly, it is of interest to develop approaches that overcome at least some of the above-described problems with respect to solubility and aggregation of crude and final peptide products. Of particular interest would be the development of such approaches for peptide thioesters or selenoesters. The present invention satisfies these needs, as well as others.

SUMMARY OF THE INVENTION

The invention is directed to water-soluble thioester and selenoester compounds, generators thereof, as well as methods for making and using the same. The subject thioester and selenoester compounds are characterized by including an amino acid synthon joined to a water-soluble polymer through a thioester or a selenoester. Solid phase polypeptide synthesis (SPPS) resins and protocols for generating the subject compounds are also provided. The subject water-soluble thioester and selenoester compounds find use in a variety of different applications, including thioester or selenoester mediated chemical ligation reactions.

BRIEF DESCRIPTION OF THE FIGURES

The invention will be more fully understood by reference to the following drawings, which are for illustrative purposes only.

Figure 1:
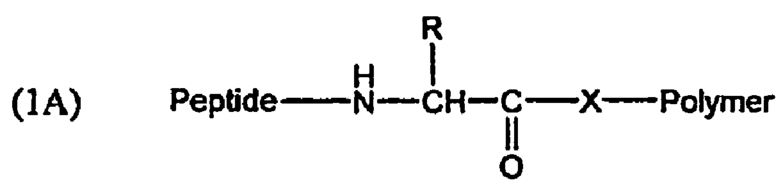
FIG. 1 depicts four general compositions in accordance with the invention.
Figure 1:
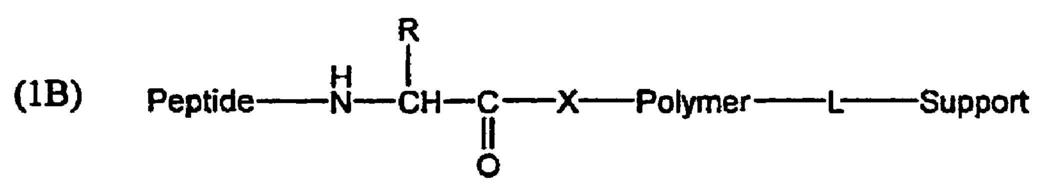
Figure 1:
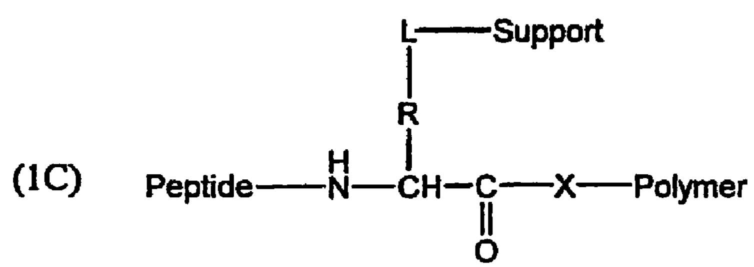
Figure 1:
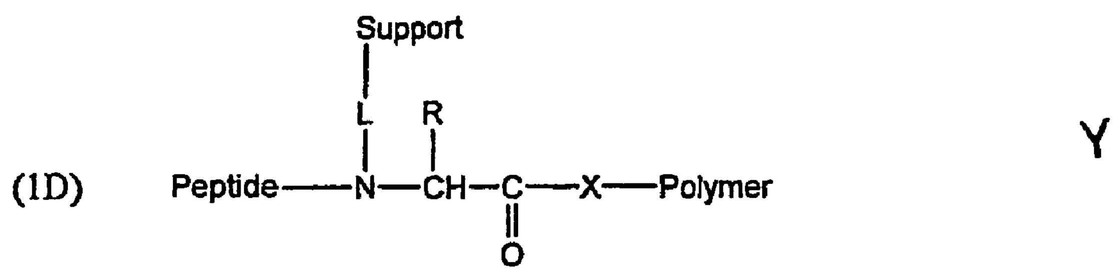

Before the invention is further described in detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims. Also, as used herein and in the appended claims, the singular forms "a", "and", and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DESCRIPTION OF THE SPECIFIC EMBODIMENTS

The invention is directed to water-soluble thioester and selenoester compounds, generators thereof, and related methods for their production and use. The subject thioester and selenoester compounds of the invention are characterized by including an amino acid synthon that is joined to a water-soluble polymer through a thioester or a selenoester. The subject thioester and selenoester compounds can be readily made using thioester and selenoester generators of the invention.

The thioester and selenoester generators of the invention comprise an amino acid synthon having an N-terminal group joined to a C-terminal group through an organic backbone, where the C-terminal group is joined to a water-soluble polymer through a thioester or selenoester moiety, and where the amino acid synthon is joined to a support through a linker that is cleavable under non-nucleophilic conditions. Cleavage of the linker under non-nucleophilic conditions generates the desired water-soluble thioester and selenoester compounds free of the support.

Such water-soluble thioester and selenoester compounds and their generators find a broad range of use in a variety of different applications, including wide applicability in organic synthesis. For instance, water-soluble thioester and selenoester compounds of the invention that comprise peptides or polypeptides are particularly useful in peptide and polypeptide synthesis techniques that employ thioester- and/or selenoester-mediated ligation, including native chemical ligation.

The invention offers many advantages over the prior art in that the solid phase synthesis resins and protocols of the invention yield water-soluble thioester and selenoester compounds, which are easily purified and/or manipulated. The compounds of the invention also can improve the overall efficiency and yields of complex multi-step ligation or conjugation schemes.

In further describing the subject invention, representative thioester and selenoester compounds are described first in greater detail, followed by a description of representative compositions and methods for making and using the subject compounds.

Water-soluble Thioester and Selenoester Compounds

The water-soluble thioester and selenoester compounds of the invention include an amino acid synthon having an N-terminal group joined to a C-terminal group through an organic backbone, where the C-terminal group is joined to a water-soluble polymer through a thioester or selenoester. The thioester or selenoester may or may not be sterically hindered. The organic backbone may comprise a target molecule of interest, such as an amino acid, peptide, polypeptide or other organic compound of interest.

In certain embodiments, the water-soluble thioester or selenoester compounds bear an N-terminal group having a moiety selected from: (i) a functional group protected with a protecting group, (ii) an unprotected functional group, or (iii) an unprotected group that is substantially unreactive. A preferred N-terminal group comprises a moiety selected from a free amine, an amine protected with a nucleophile-stable amine protecting group, and an unprotected group lacking a reactive functionality, such as a unreactive alkyl or aryl capping moiety that may be linear, branched, substituted or unsubstituted. Another preferred embodiment employs an N-terminal group that is capable of supporting chemical ligation, and may be protected or unprotected.

In certain embodiments, the water-soluble thioester or selenoester compounds of the invention possess a C-terminal group bonded to a thioester or selenoester that includes a water-soluble polymer, where the water-soluble polymer component will preferably include a repeat unit comprising a polyalkylene oxide, a polyamide alkylene oxide, or derivatives thereof. Most preferably, the polyalkylene oxide and polyamide alkylene oxide include an ethylene oxide repeat unit of the formula —($CH_2$—$CH_2$—O—. The water-soluble polymer may be linear or branched, including dendrimer structures. In a preferred embodiment, the water-soluble polymer will have a net charge under physiological conditions. Depending on the construct employed, the net charge can be positive, neutral or negative. The most preferred water-soluble polymers of the invention are mono-disperse, i.e., a single molecular species as distinguished from hetero-disperse compounds composed of multiple different molecular species. Utilization of a mono-disperse water-soluble polymer has the advantage of permitting the construction of compounds that are also mono-disperse. Most preferably, the water-soluble polymer will have a discrete molecular weight that is sufficient to permit separation of the compound from a corresponding thioester or selenoester compound that is missing the water-soluble polymer. In other embodiments, the C-terminal group includes a moiety chosen from a sterically hindered thioester or sterically hindered selenoester, where the sterically hindered thioester or selenoester includes a water-soluble polymer. Preferably, the water-soluble polymer will include a repeat unit comprising a polyalkylene oxide, a polyamide alkylene oxide, or derivatives thereof. Here again, it is most preferable that the water-soluble polymer has a discrete molecular weight that is sufficient to provide for separation from a corresponding sterically hindered thioester or sterically hindered selenoester compound that is missing the water-soluble polymer.

By "amino acid synthon" is intended to refer to a structural unit within a molecule, the structural unit including at least one amino acid or amino acid residue having an N-terminus comprising or extending from the alpha nitrogen of the amino acid or amino acid residue, a C-terminus comprising or extending from the alpha carbonyl of the amino acid or amino acid residue and an organic backbone that joins the N- and C-termini and is substituted or unsubstituted with one or more side chains, where the structural unit can be formed and/or assembled by known or conceivable synthetic operations.

Examples of amino acid synthons are unprotected and partially or fully protected amino acids and peptides having a modified or unmodified alpha amino terminus (N-terminus) and/or a modified or unmodified alpha carbonyl terminus (C-terminus), including un-activated and activated esters thereof, as well as salts thereof, such as trifluoroacetic acid (TFA) salts. It also includes variable forms thereof in which the pendant N- and/or C-termini comprise terminal groups other than an alpha amino or carbonyl moiety, such as other amino acid non-functional and functional groups, one or more protecting groups, halogens, azides, conjugates, organic moieties other than an amino acid, a target molecule of interest or components thereof, depending on the intended end use.

The term "amino acid" means any of the 20 genetically encodable amino acids, non-encoded amino acids, and analogs and derivatives thereof, including α-amino acids, β-amino acids, γ-amino acids, and other compounds having at least one N-terminal amino functionality and at least one C-terminal carboxyl (or carbonyl) functionality thereon. L- and D-forms of the chiral amino acids are also contemplated. The terms "peptide", "polypeptide" and "protein", which may be used interchangeably herein, refer to an oligomeric or polymeric form of amino acids, which can include coded and non-coded amino acids, chemically or biochemically modified or derivatized amino acids and polypeptides having modified peptide backbones.

In the context of an amino acid synthon, an "organic backbone" may comprise the alpha, beta and/or gamma carbons of a single amino acid residue, and other substituents, including additional backbone carbons and/or heteroatoms, as well as alpha amino groups of an amino acid or residue that are substituted or unsubstituted (amides included), alpha carbonyls that are substituted or unsubstituted (carboxyls, carboxyesters and amide bonds included), and may comprise an amino acid residue or peptide, as well as organic side chains. Representative organic side chains are those of amino acids. The organic backbone typically comprises a part of or most of a target molecule of interest.

The organic backbone may be fully protected, partially protected or unprotected depending on the intended end use. This includes organic backbones that have one or more side chains bearing a functional group protected with a protecting group, as well as different protecting groups thereon that are removable orthogonal conditions. Such a configuration is particularly convenient where the organic backbone is constructed using solution or solid phase chain assembly methods. For instance, the organic backbone may include a peptide chain containing amino acid residues bearing protected functional groups removable under conditions orthogonal to removal of an N-terminal protecting group during peptide elongation cycles. In other instances, the organic backbone may contain one or more side chains bearing a functional group protected with a protecting group that is removable under the same conditions as the N-terminal protecting group. Alternatively, the organic backbone may contain one or more side chain functional groups that are substantially non-reactive to conditions used for generating or manipulating a target molecule during elongation or elaboration cycles, and/or side chains that would otherwise be reactive but are protected with protecting groups that are orthogonal to such generating or manipulating conditions.

The term "orthogonal" as used herein with respect to protecting groups, linkers and other groups means that the specific group or linker is removable or cleavable under conditions that do not result in removal or cleavage of an "orthogonal" group or linker. Thus, for example, where one protecting group is nucleophile-stable and another is nucleophile-labile, such groups are said to be "orthogonal". For instance, when the organic backbone is made to contain cysteine amino acid residues, the side chain thiol can be protected with an acetamidomethyl (Acm) or Picolyl group, which are stable to basic conditions (e.g., typical conditions for Fmoc-compatible cycles) or acidic conditions (e.g., typical Boc-compatible cycles). Protecting groups like Acm- and Picolyl also are removable under conditions orthogonal to carbonyl protecting groups such as Allyl or ODMab, as well as to primary amine protecting groups such as Alloc. Where the organic backbone contains side chain functional groups that are substantially unreactive, protection of those groups is typically not required. Examples of side chain groups that are substantially unreactive include saturated alkyl groups, chains and alcohols, and other such groups can be selected depending on the conditions employed.

As described above, the thioester and selenoester compounds of the invention may have a modified or unmodified alpha amino terminus (N-terminus). In a preferred embodiment, the thioester and selenoester compounds of the invention have an N-terminal group that comprises an amino acid. Any amino acid can be used. In certain embodiments, the amino acid is capable of supporting chemical ligation.

Chemical ligation involves the selective covalent linkage of a first chemical component to a second chemical component. Orthogonally reactive functional groups present on the first and second components can be used to render the ligation reaction chemoselective. For example, chemical ligation of peptides and polypeptides involves the chemoselective reaction of peptide or polypeptide segments bearing compatible, mutually reactive C-terminal and N-terminal amino acids. Several different chemistries have been utilized for this purpose, examples of which include native chemical ligation (Dawson, et al., Science (1994) 266:776-779; Kent, et al., WO 96/34878; Kent et al., U.S. Pat. No. 6,184,344), extended general chemical ligation (Kent, et al., WO 98/28434; and Kent et al., U.S. Pat. No. 6,307,018); extended native chemical ligation (Botti et al., WO 02/20557); oxime-forming chemical ligation (Rose, et al., J. Amer. Chem. Soc. (1994) 116:30-33), thioester forming ligation (Schnölzer, et al., Science (1992) 256:221-225), thioether forming ligation (Englebretsen, et al., Tet. Letts. (1995) 36(48):8871-8874), hydrazone forming ligation (Gaertner, et al., Bioconj. Chem. (1994) 5(4):333-338), and thiazolidine forming ligation and oxazolidine forming ligation (Zhang, et al., Proc. Natl. Acad. Sci. (1998) 95(16):9184-9189; Tam, et al., WO 95/00846) or by other methods (Yan, L. Z. and Dawson, P. E., "Synthesis of Peptides and Proteins without Cysteine Residues by Native Chemical Ligation Combined with Desulfurization," J. Am. Chem. Soc. (2001) 123:526-533; Gieselnan et al., Org. Lett. (2001) 3(9):1331-1334; Saxon, E. et al., "Traceless" Staudinger Ligation for the Chemoselective Synthesis of Amide Bonds. Org. Lett. (2000) 2:2141-2143). In many embodiments, chemical ligation methods of interest employ amide-forming chemical ligation, such as native chemical ligation and extended native chemical ligation.

By "capable of supporting chemical ligation" is intended to refer to a moiety that is in a form which can be directly employed in a chemical ligation reaction, or can be converted to a moiety for use in a chemical ligation reaction. In many situations, a moiety capable of supporting chemical ligation will be in a form that must be converted for a ligation reaction to proceed. For instance, when a water-soluble thioester or selenoester compound of the invention is employed for making a target molecule bearing an N-terminal amino acid capable of supporting chemical ligation in combination with a C-terminal thioester or selenoester having a water-soluble polymer, the N-terminal amino acid is typically protected by a method to avoid intramolecular cyclization unless such cyclization is desired. By protecting the N-terminal amino acid in this way, such a target molecule can be used for a thioester or selenoester-mediated chemical ligation reaction, such as native or extended native chemical ligation, followed by removal of the N-terminal protection for subsequent native or extended native chemical ligation reaction cycles (e.g., sequential native or extended native chemical ligation). In some instances, however, intramolecular cyclization may be desired, which is particularly useful for making cyclic products, such as cyclic peptides. N-terminal amino acids, such as serines, that are capable of being converted to bear an aldehyde moiety by mild oxidation or reductive alkylation is another example, and are particularly useful in Schiff-base mediated chemical ligation reactions. In other chemical ligation reactions, the N-terminal amino acid can be provided in a ready-to-use chemical ligation form, such as when the N-terminal amino acid bears an azide, halogen or aminooxy group for other chemical ligation reactions.

Where the N-terminal group comprises an amino acid capable of supporting native or extended native chemical ligation, the amino acid comprises a side chain bearing an atom selected from sulfur and selenium. Examples of amino acids suitable for use in native chemical ligation include an alpha-carbon side chain bearing a sulfur or selenium atom, such as cysteine, homocysteine, selenocysteine, homoselenocysteine and respective protected forms thereof. Examples of amino acids suitable for use in extended native chemical ligation comprise an alpha-nitrogen side chain bearing a sulfur or selenium atom, which include the alpha-nitrogen substituted 2 or 3 carbon chain alkyl or aryl thiol and selenol auxiliaries, and protected forms thereof as described in Botti et al., WO 02/20557. As can be appreciated, an N-terminal amino acid capable of supporting native or extended native chemical ligation can be protected using a protecting group for the alpha-nitrogen, the side chain sulfur or selenium, or a combination of both, including cyclic protection strategies employing an N-terminal thioproline or extended native chemical ligation alpha-nitrogen substituted auxiliary. The thioester and selenoester generators of the invention preferably employ an amino acid bearing a side chain sulfur or selenium group that is protected.

As described above, the C-terminal group of the thioester and selenoester compounds of the invention includes an ester of sulfur or selenium, i.e., thioester and selenoester, at the C-terminal end of the amino acid synthon. The ester is further characterized in that it includes a water-soluble polymer bonded, either directly or indirectly through a linker or spacer, to the sulfur or selenium atom of the ester. The ester moiety may include any linker or spacer group compatible with the thioester or selenoester group, including, but not limited to, aryl, benzyl, and alkyl groups that may be linear, branched, substituted or unsubstituted, and which includes amino acid, peptide and other organic thioester or selenoester moieties. Representative examples include 3-carboxy-4-nitrophenyl thioesters, benzyl thioesters and selenoesters, mercaptopropionyl thioesters and selenolpropionyl selenoesters, and mercaptopropionic acid leucine thioesters and selenolpropionic acid leucine selenoesters (See, e.g., Dawson et al., Science (1994) 266:776-779; Canne et al. Tetrahedron Lett. (1995) 36:1217-1220; Kent, et al., WO 96/34878; Kent, et al., WO 98/28434; Ingenito et al., J. Am. Chem. Soc (1999) 121(49):11369-11374; and Hackeng et al., Proc. Natl. Acad. Sci. U.S.A. (1999) 96:10068-10073), that are linked or derivatized and joined to a water-soluble polymer of the invention directly or indirectly though a spacer.

In certain embodiments, the C-terminal group comprises the formula J-CH($R_2$)—C(O)—X—$R_3$, where J comprises a residue of the organic backbone; $R_2$ comprises any side chain group; X is sulfur or selenium; and $R_3$ is any thioester or selenoester compatible group that includes a water-soluble polymer group. In this formula, $R_2$ may be any organic side chain compatible with thioesters or selenoester, such as a side chain of an amino acid, and $R_3$ may be selected from a group of the formula —C($R_7$)($R_8$)-U-Polymer, where $R_7$ and $R_8$ each individually are selected from hydrogen, linear, branched, substituted and unsubstituted alkyl, aryl, heteroaryl and benzyl groups, and where U is a linker or spacer that may be present or absent, and "Polymer" is a water-soluble polymer. The U group may include linear or branched moieties comprising one or more repeat units employed in the water-soluble polymer, natural or unnatural amino acids or derivatives thereof, as well as aliphatic moieties, including alkyl, aryl, heteroalkyl, heteroaryl, alkoxy and the like, which preferably contain up to 18 carbon atoms or even an additional polymer chain.

The formula J-CH($R_2$)—C(O)—X—$R_3$ also includes C-terminal groups that comprise a sterically hindered thioester or selenoester, where $R_2$ and/or $R_3$ may be a group that sterically hinders the thioester or selenoester moiety —C(O)—X—. By "sterically hindering" or "sterically hindered" is intended to refer to a group or groups that prevent or help prevent hydrolysis or self-induced aminolysis associated with the —C(O)—X— moiety. Accordingly, in this embodiment, $R_2$ may be selected from a branching group having the formula —C($R_4$)($R_5$)($R_6$), where $R_4$, $R_5$ and $R_6$ each individually are selected from hydrogen and linear, branched, substituted and unsubstituted alkyl, aryl, heteroaryl and benzyl groups, with the proviso that when $R_3$ is devoid of a sterically hindering group, then two or more of $R_4$, $R_5$ and $R_6$ are selected from linear, branched, substituted and unsubstituted alkyl, aryl, heteroaryl and benzyl groups, and $R_3$ may be selected from a group of the formula —C($R_7$)($R_8$)-U-Polymer, where $R_7$ and $R_8$ each individually are selected from hydrogen and linear, branched, substituted and unsubstituted alkyl, aryl, heteroaryl and benzyl groups, with the proviso that when $R_2$ is devoid of a sterically hindering group, then one or more of $R_7$ and $R_8$ are selected from linear, branched, substituted and unsubstituted alkyl, aryl, heteroaryl and benzyl groups for sterically hindered thioester or sterically hindered selenoester, and where U and Polymer are as described above.

As described above, a feature of the thioester and selenoester moieties of the subject compounds is the presence of a water-soluble polymer. In other words, the thioester or selenoester moieties of the subject compounds include a water-soluble polymer moiety. Typically, the water-soluble polymer moiety is bonded either directly or through a linking or spacer group to the sulfur or selenium atom of the ester moiety. By "water-soluble polymer" is intended to mean a polymer that is soluble in water and has an atomic molecular weight greater than about 500 Daltons. The water-soluble polymer may have an effective hydrodynamic molecular weight of greater than 1000 Da, with 1,000 to about 500,000 Da, and more preferably, from about 1,000 to about 100,000 Da, and most preferably, from about 1,500 to about 50,000 Da. By "effective hydrodynamic molecular weight" is intended to refer to the effective water-solvated size of a polymer chain as determined by aqueous-based size exclusion chromatography (SEC). When the water-soluble polymer contains polymer chains having polyalkylene oxide repeat units, such as ethylene oxide repeat units, each chain may have an atomic molecular weight of between about 200 and about 80,000 Da, such as between about 500 and about 40,000 Da, with 500 to about 5,000 Da being the size range in certain embodiments. Unless referred to specifically, molecular weight is intended to refer to atomic molecular weight.

The water-soluble polymer component can have a wide range of molecular weight, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above are well known, particularly the polyalkylene oxide based polymers such as polyethylene glycol "PEG" (See. e.g., "Poly (ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M., Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964 and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

In certain embodiments, the water-soluble polymer component comprises a polyalkylene oxide, polyamide alkylene oxide, or derivatives thereof. A more typical polyalkylene oxide and polyamide alkylene oxide comprise an ethylene oxide repeat unit of the formula —$CH_2$—$CH_2$—O—. A representative polymer component is a polyamide having a molecular weight greater than about 500 Daltons of the formula —[C(O)-ϕ-C(O)—NH-ψ-NH]$_{n5}$— or —[NH-ψ-NH—C(O)-ϕ-C(O)]$_{n5}$—, where ϕ and ψ are divalent radicals that may be the same or different and may be branched or linear, and $n_5$ is a discrete integer from 2 to 100, and more preferably from 2 to 50, and where either or both of ϕ and ψ comprises a biocompatible, substantially non-antigenic water-soluble repeat unit that may be linear or branched. In certain embodiments, the water-soluble repeat unit comprises an ethylene oxide of the formula —($CH_2$—$CH_2$—O)— or —O—$CH_2$—$CH_2$)—. The number of such water-soluble repeat units can vary significantly, but the more preferred number of such units is from 2 to 500, 2 to 400, 2 to 300, 2 to 200, 2 to 100 and sometimes 2 to 50. An example of such an embodiment is where one or both of ϕ and ψ is selected from: —(($CH_2$)$_{n6}$—($CH_2$—$CH_2$—O)$_{n7}$($CH_2$)$_{n6}$—)— or —(($CH_2$)$_{n6}$—(O—$CH_2$—$CH_2$)$_{n7}$—($CH_2$)$_{n6}$—)—, where $n_6$ is 1 to 6, 1 to 5, 1 to 4 and most preferably 1 to 3, and where $n_7$ is 2 to 50, 2 to 25, 2 to 15, 2 to 10, 2 to 8 and most preferably 2 to 5. An example of a highly preferred embodiment is where ϕ is —($CH_2CH_2$)—, and where ψ is —($CH_2$—($CH_2$—$CH_2$—O)$_3$—$CH_2$—$CH_2$—$CH_2$)— or —($CH_2CH_2$—$CH_2$—(O—$CH_2$—$CH_2$)$_3$—$CH_2$)—. Preferred water-soluble polymers and exemplary synthesis approaches, including those of the formula —[C(O)-ϕ-C(O)—NH-ψ-NH]$_{n5}$— or —[NH-ψ-NH—C(O)-ϕ-C(O)]$_{n5}$— are described in PCT Publication Nos. WO 02/19963 and WO 02/20033.

The more preferred water-soluble polymer is one produced in total by stepwise synthesis. This permits construction of polymers having a precise molecular weight and defined structure. In contrast, normal polymer synthesis, which is a polymerization process, results in a mixture in which chains are of differing lengths. Thus, there is a distribution of molecular weights and sizes that are difficult if not impossible to separate. The ability to control molecular purity is advantageous in that thioester or selenoester compounds of the invention can be constructed to include a water-soluble polymer that is mono-disperse, i.e., a single molecular species as distinguished from hetero-disperse compounds composed of multiple different molecular species. This represents a significant advantage in that variable properties resulting from heterogeneous compounds can be avoided, including contamination with side-reaction byproducts, and thus, only those thioester or selenoester compounds with the most preferred properties such as high purity can be prepared and isolated with relative ease.

As noted above, water-soluble polymers that are made in total by stepwise assembly can be made as mono-disperse, for example, the preferred polyamide ethylene oxides of the invention, such as those of the formula —[C(O)-ϕ-C(O)—NH-ψ-NH]$_{n5}$— or —[NH-ψ-NH—C(O)-ϕ-C(O)]$_{n5}$—. Such polyamide polymers combine the advantages of stepwise chain assembly along with the precision length, flexibility and water-solubility properties (sometimes referred to as "pPEG", "precise length polymer" or "PLP"). Such PLP moieties can be synthesized in any of a variety of ways. Such moieties are, however, preferably produced using a solid phase stepwise chain assembly of units. The use of such an assembly process permits the moieties of a preparation to have a defined and homogeneous structure, as to their length, the nature of their ψ and ϕ substituents, the position(s) (if any) of branch points, and the length, ψ and ϕ substituents, and position(s) of any branches. Methods of particular interest for synthesis of such PLP moieties is described in, for example, PCT Publication Nos. WO 02/19963, WO 02/20033, and WO 00/12587 (which references refer to the compound —[NH-ψ-NH—C(O)-ϕ-C(O)]— as —[NH—Y—NH—C(O)—X—C(O)]—).

Thus, another preferred embodiment is one where the water-soluble polymer of the water-soluble thioester and selenoester compounds of the invention is mono-disperse (i.e., a molecularly homogenous composition containing a single and structurally defined molecular species of interest). Also, it is preferred that the target molecule of interest comprising an amino acid synthon be monodisperse as well for example, as peptides and proteins can be made in total by chemical synthesis, they can be made mono-disperse as well. Such compounds have the advantage of being highly pure and avoid the problems of purification and analytical characterization such as when hetero-disperse polymers are employed. Such compounds are advantageous in terms of reproducible synthesis and the like as well, for example, a single molecular species as opposed to mixtures typical of polymers made by polymerization processes, e.g., polyethylene glycol (PEG).

Accordingly, properties of the water-soluble thioesters and selenoesters of the invention can be modified by precisely adjusting the molecular weight, structure, hydrophilicity, hydrophobicity and charge of the water-soluble polymer. In particular, in addition to increasing the water hydration and molecular weight of a target compound of interest to improve its synthesis and handling properties, the water-soluble polymer of the thioester or selenoester can render the target compound to have a precise molecular weight, structure, hydrophilicity, hydrophobicity and charge that can be adjusted for a given solution or solid phase system to modulate the handling properties and/or subsequent manipulation and properties of a target compound of interest. A preferred embodiment of the invention is thus directed to water-soluble thioester and selenoester compounds and methods that combine the above features.

By way of example, a preferred water-soluble thioester and selenoester compound of the present invention comprises an amino acid synthon having an N-terminal group joined to a C-terminal group through an organic backbone, and comprises the formula:

(1)

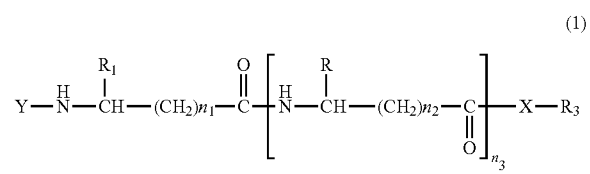

wherein Y is a target molecule of interest that may be present or absent; $R_1$ is hydrogen or an organic side chain; each R individually is hydrogen or an organic side-chain; $n_1$ and $n_2$ each are from 0 to 2; $n_3$ is from 0 to 100; X is sulfur or selenium; and $R_3$ is any group compatible with thioesters or selenoesters that includes a water-soluble polymer, as described above.

In compounds of structure (1), the group Y may comprise any molecule of interest including, for example, an amino acid, peptide, polypeptide, nucleic acid, lipid, carbohydrate, combinations thereof and the like. In many embodiments, Y groups are peptides. In a preferred embodiment, Y comprises an N-terminal group that may be protected or unprotected. Where the N-terminal group of the target molecule Y is designed as an intermediate for subsequent chemical ligation reactions, Y will preferably be composed of an N-terminal amino acid that is capable of supporting chemical ligation. Examples of N-terminal amino acids capable of supporting chemical ligation include cysteine, or an N-alpha amino substituted with an auxiliary side chain bearing a thiol or selenol for general or extended native chemical ligation. For N-terminal ligation groups, the thiols, selenols or other nucleophiles may protected with protecting groups such as Acm or benzyl derivatives. Alternatively, the N-alpha amino group of may be protected (e.g., Boc-, Fmoc, Nsc etc.). In some instances, both the N-alpha amino and the side chain functionalities are protected, e.g., by forming a cleavable cyclic structure such as a thioproline in the case of cysteine. Where Y comprises an N-terminal group that is substantially non-reactive, such as a linear, branched, substituted or unsubstituted aliphatic or other capping group, then no N-terminal protecting group is needed. Alternatively, a reactive group may be present on the N-terminal group, but is generally chosen so as not to react with the C-terminal thioester or selenoester, except where thioester- or selenoester-mediated intramolecular cyclization of the compound is desired. As can be appreciated, other protecting groups may be present on the compound for subsequent elaborations, such as one or more residual protecting groups on the side chains R and $R_1$ depending on the intended end use of the thioester or selenoester compound. Such protecting groups, if present can be cleavable under identical or orthogonal conditions relative to other protecting groups that may be present.

The R and $R_1$ groups of the structure (1) may each individually comprise hydrogen or any organic side chain, for example, a side chain of an amino acid. The group $R_3$ may comprise any group that is compatible with a thioester or selenoester, where the group includes a water-soluble polymer as described above. As noted above, $n_3$ in structure (1) is from 0 to 100, and is preferably 0 to 100 when Y is absent, or when Y is present is typically less than 100 depending on the nature of Y. For example, when Y is a peptide, then the total length of the thioester or selenoester compound will typically be about or less than 100 amino acids.

In another embodiment, and by way of example, a sterically hindered water-soluble thioester or selenoester compound comprising an amino acid synthon having an N-terminal group joined to a C-terminal group through an organic backbone, comprises the formula:

(2)

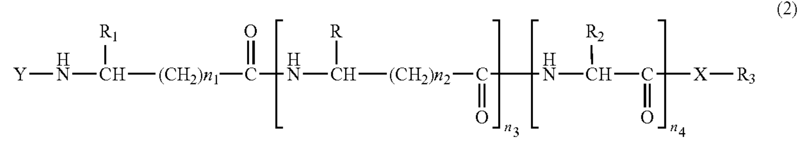

wherein Y is a target molecule of interest that may be present or absent; each $R_1$, R and $R_2$ individually is any side chain group and may be the same or different; $n_1$ and $n_2$ each individually is 0, 1 or 2; $n_3$ is 0 to 100; $n_4$ is 0 to 1; X is sulfur or selenium; and $R_3$ is any thioester or selenoester compatible group that includes a water-soluble polymer; and wherein at least one of R, $R_1$, $R_2$ and $R_3$ includes a group that sterically hinders the thioester or selenoester moiety —C(O)—X—. For example, when $n_2$ and $n_4$ are 0, R and/or $R_3$ would include a sterically hindering group. In another example, when $n_1$, $n_3$ and $n_4$ are 0, R and/or $R_3$ would include a sterically hindering group. Yet another example is where $n_2$ is 1 or 2, and $n_3$ is one or more, then $R_2$ and/or $R_3$ would include a sterically hindering group.

In the compounds of the structure (2), $n_3$ and the Y group are the same as described above for compounds of the structure (1). Similarly, the group R, $R_1$ and $R_2$ groups of the structure (2) may each individually comprise hydrogen or any organic side chain, for example, a side chain of an amino acid, with the proviso that at least one of R, $R_1$, $R_2$ and $R_3$ includes a group that sterically hinders the thioester or selenoester moiety —C(O)—X— as described above. The group $R_3$ may comprise any group that is compatible with a thioester or selenoester, where the group includes a water-soluble polymer as described above, again with the proviso that at least one of R, $R_1$, $R_2$ and $R_3$ includes a group that sterically hinders the thioester or selenoester moiety —C(O)—X— as described above. For instance, sterically hindering groups usable for R, $R_1$ and $R_2$ include, by way of example, branched alkane, cycloalkane, alkyl-substituted aryl and heteroaryl groups, and combinations thereof. Such sterically hindering groups may comprise the formula $—C(R_4)(R_5)(R_6)$ as described above, where $R_4$, $R_5$ and $R_6$ each individually includes hydrogen, a linear, branched, cyclic substituted or unsubstituted alkyl, aryl, heteroaryl or benzyl group, and at least two of $R_4$, $R_5$ and $R_6$ each individually include a linear, branched, cyclic substituted or unsubstituted alkyl, aryl, heteroaryl or benzyl group.

Similarly, the $R_3$ group of structure (2) may be selected from a group of the formula $—C(R_7)(R_8)$-U-Polymer, where $R_7$ and $R_8$ each individually are selected from hydrogen and linear, branched, substituted and unsubstituted alkyl, aryl, heteroaryl and benzyl groups, with the proviso that when R, $R_1$, and $R_2$ are devoid of a sterically hindering group, then one or more of $R_7$ and $R_8$ are selected from linear, branched, substituted and unsubstituted alkyl, aryl, heteroaryl and benzyl groups for sterically hindered thioester or sterically hindered selenoester, and where U is a linker or spacer that may be present or absent, and "Polymer" is a water-soluble polymer. The U group may include linear or branched moieties comprising one or more repeat units employed in the water-soluble polymer, natural or unnatural amino acids or derivatives thereof, as well as aliphatic moieties, including alkyl, aryl, heteroalkyl, heteroaryl, alkoxy and the like, which preferably contain up to 18 carbon atoms or even an additional polymer chain. The formula $—C(R_7)(R_8)$-U-Polymer also may be represented as the formula $—C(R_7)(R_8)$-Polymer, where U is missing or provided by the component Polymer. Other groups providing steric hindrance for the thioester or selenoester moiety may also be used.

Synthesis of the Subject Water-soluble Thioester and Selenoester Compounds, and Generator Thereof The subject thioester and selenoester compounds of the invention may be synthesized, in general terms, by: (a) providing a thioester or selenoester generator comprising a support that is joined through a linker to an amino acid synthon, where the linker is cleavable under non-nucleophilic conditions, and where the amino acid synthon comprises a thioester or selenoester joined to a water-soluble polymer; and (b) cleaving the linker under non-nucleophilic conditions to release the amino acid synthon from the support.

The amino acid synthon, when joined to the support, may comprise a target molecule of interest that is lacking one or more reactive functional groups. As used herein, the term "lacking reactive functional groups" is intended to mean a group or radical in which such reactive functional group is entirely absent, as well as a group or radical that contains a protected functional group that would otherwise be reactive but for the presence of the protecting group. For example, where the support-bound amino acid synthon and its organic backbone includes side chains or other moieties bearing functional groups (e.g., functional groups of a target peptide), one or more, and preferably all of such groups will typically be protected when a target molecule is synthesized on the support (e.g., SPPS). Depending on the choice of protecting groups, the cleavage reaction may provide for their removal. Alternatively, one or more of the protecting groups may be retained if they are removable under conditions that differ from the cleavage reaction, i.e., orthogonal protection.

Accordingly, a thioester or selenoester product of the above method of the invention may be fully, partially or totally unprotected following cleavage and release from the support, and be soluble under aqueous conditions. The organic backbone of the amino acid synthon may be associated with a target molecule and may comprise an amino acid, peptide or polypeptide with one or more side chains bearing protected or unprotected functional groups, and the N-terminal group of the amino acid synthon may itself comprise protected or unprotected amino acid groups as also described above. The N-terminal group also may be capable of supporting chemical ligation, and may comprise an amino acid with a protected or unprotected side chain functionality capable of participating in native chemical ligation, extended chemical ligation or other ligation technique to form an amide or other bond.

Cleavage of the linker to form the freed thioester or selenoester compound may be carried out under various conditions according to the nature of the linker used and the orthogonality of protecting groups present in the composition with respect to the linker. Where an N-terminal protecting group is present, cleavage of the linker may be carried out under conditions orthogonal to removal of the N-terminal protecting group, as well as orthogonal to any protecting groups for side chain groups associated with the amino acid synthon, such that the freed thioester or selenoester compound is fully or partially protected. Such orthogonal conditions may include, for example, linker cleavage under acid conditions where the N-terminal protecting group is acid stable. Linker cleavage may alternatively involve non-orthogonal conditions that also result in removal of the N-terminal protecting group and/or one or more amino acid side chain protecting groups that may be present on the organic backbone, such that the freed thioester or selenoester compound is partially protected or unprotected all together. Selection of various protecting groups and orthogonality of removal of protecting groups with respect to linker cleavage may be made based on desired synthetic schemes and solubility characteristics for the freed thioester or selenoester compounds.

In the subject thioester or selenoester generators of the invention, the linker may be joined to the amino acid synthon at any one of several positions. For instance, the linker may be joined to the backbone (e.g., backbone heteroatom such as nitrogen) or side chain (e.g., pendant functional group of a side chain such as an amino or carboxylate group) of the amino acid synthon. Alternatively, the linker may be joined to the water-soluble polymer of the amino acid synthon. Moreover, the linker may comprise any cleavable group capable of anchoring the amino acid synthon to the support material, with the proviso that the linker is cleavable under non-nucleophilic conditions. Cleavage under non-nucleophilic conditions is important and desirable as nucleophiles can destroy the thioester or selenoester.

The use of linker groups in solid phase synthesis is well known, and various linker groups are usable with the invention. For instance, the linker may be bifunctional, and may serve as a spacer with a cleavable group on one end, and a group such as a carboxyl group at the other end that can be activated to allow coupling to a functionalized support material. The linker can be a preformed linker or may be prepared on a support material.

Suitable linkers include, for example, PAL, XAL, PAM, RINK, SCAL and Sieber-based linker systems (e.g., PAL (5-(4'-aminomethyl-3',5'-dimethoxyphenoxy)valeric acid, XAL (5-(9-aminoxanthen-2-oxy)valeric acid), 4-(alpha-aminobenzyl)phenoxyacetic acid, 4-(alpha-amino-4'-methoxybenxyl)phenoxybutyric acid, p-alkoxybenzyl (PAB) linkers, photolabile o-nitrobenzyl ester linkers, 4-(alpha-amino-4'-methoxybenzyl)-2-methylphenoxyacetic acid, 2-hydroxyethylsulfonylacetic acid, 2-(4-carboxyphenylsulfonyl)ethanol, (5-(4'-aminomethyl-3',5'-dimethoxyphenoxy)valeric acid) linkers, WANG hydroxymethyl phenoxy-based linkers, RINK trialkoxybenzydrol and trialkoxybenzhydramine linkers, PAM phenylacetamidomethyl, SCAL-type safety catch acid labile linkers and Sieber aminoxanthenyl linkers).

Derivatives of such linkers and other linker systems may also be used. These linker systems are cleavable under well known acidolysis conditions (typically trifluoroacetic acid (TFA) or hydrogen fluoride (HF)), UV photolysis (λ≈350 nm) conditions or catalytic hydrogenation conditions. Several of the above linker systems are commercially available as preformed on resin and glass supports.

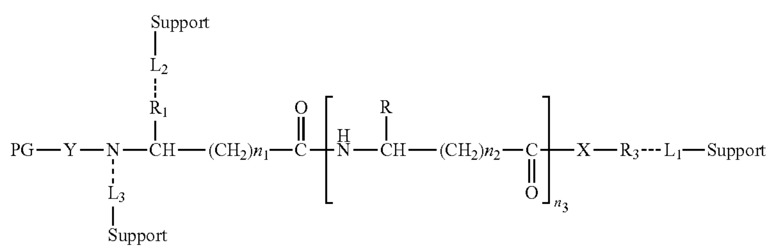

In the subject generators, the linker is covalently anchored to a support as described further below. Suitable supports may comprise, for example, matrices, surfaces, resins or other solid phase supports that are compatible with peptide synthesis or other synthetic schemes associated with a target molecule. The support may comprise a functionalized glass, an organic polymer or other compatible material. As such, the support of the thioester and selenoester generators of the invention comprises a solid phase, matrix or surface compatible with organic synthesis strategies. Preferable supports are those compatible with peptide synthesis. A variety of such supports are well known, and can be employed, including those described in further detail herein. Examples include supports or resins comprising cross-linked polymers, such as divinylbezene cross-linked polystyrene polymers, or other organic polymers that find use for solid phase organic or peptide synthesis. Controlled porous glass (CPG) supports are another example. In general, the most preferred supports are stable and possess good swelling characteristics in many organic solvents.

The above and other suitable solid supports, linkers, their preparation and application are described in, for example, "Advanced Chemtech Handbook of Combinatorial & Solid Phase Organic Chemistry," W. D. Bennet, J. W. Christensen, L. K. Hamaker, M. L Peterson, M. R. Rhodes, and H. H. Saneii, Eds., Advanced Chemtech, 1998, and elsewhere (See, e.g., G. B. Fields et al., Synthetic Peptides: A User's Guide, 77-183, G. A. Grant, Ed., W. H. Freeman and Co., New York, 1990; NovaBiochem Catalog, 2000; "Synthetic Peptides, A User's Guide," G. A. Grant, Ed., W. H. Freeman & Company, New York, N.Y., 1992; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Fmoc Solid Phase Peptide Synthesis, A Practical Approach," W. C. Chan and P. D. White, Eds., Oxford Press, 2000).

By way of example, preferred thioester or selenoester generators of the invention comprise the formula:

(3)

wherein PG is a protecting group that maybe present or absent, Y is a target molecule of interest and may be present or absent, and when Y is absent PG is an amino protecting group that may be present or absent; $R_1$ and each R individually is hydrogen or an organic side chain; $R_3$ is a water-soluble polymer; X is sulfur or selenium; $n_1$ and $n_2$ each are from 0 to 2; $n_3$ is from 0 to 100; each $L_1$, $L_2$ and $L_3$ is a linker cleavable under non-nucleophilic conditions; and Support is a solid phase, matrix or surface; and wherein only one of $L_1$, $L_2$, and $L_3$ is present.

Compositions of formula (3) also embody thioester and selenoester generators for production of the sterically hindered water-soluble thioesters and selenoesters of the invention. Such generators comprise the formula:

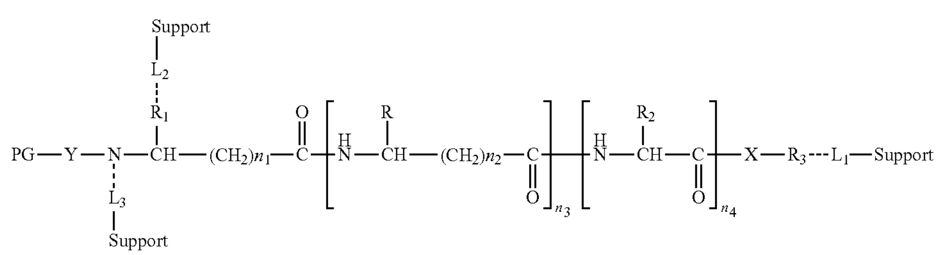

(4)

wherein PG, Y, R, $R_1$, $R_3$, X, $n_1$, $n_2$, $n_3$, $L_1$, $L_2$, $L_3$ and Support are the same as described above for the structure (3); and where $n_4$ is from 0 to 1; and $R_2$ is hydrogen or an organic side chain; and wherein only one of $L_1$, $L_2$, and $L_3$ is present.

As shown in formulas (3) and (4), the amino acid synthon comprising the water-soluble thioester or selenoester compound may be joined to the support through any one several positions, i.e., at a backbone nitrogen ($L_3$), side chain ($L_2$) or to the water-soluble polymer ($L_1$). Hence, only one $L_1$, $L_2$, and $L_3$ is present. For example, when linker $L_1$ is present the water-soluble polymer group $R_3$ of the amino acid synthon is joined to the support through linker $L_1$ (i.e., —$R_3$-$L_1$-Support), whereas the groups $L_2$-Support and $L_3$-Support are missing. Cleavage from the support produces compounds embodied in the structures (1) and (2) as described above.

Synthesis of the Water-Soluble Polymer Thioester or Selenoester Generators

The thioester and selenoester generators employed to produce the water-soluble thioester and selenoester compounds may be prepared using any convenient synthesis protocol. One type of representative and convenient protocol for synthesis of the generators is a non-nucleophile based synthesis scheme or protocol. Another type of representative and convenient protocol for synthesis of the generators is a nucleophile-based synthesis scheme or protocol. Such schemes, protocols or approaches are particularly useful where the synthesis of a target molecule of interest, such as a peptide or polypeptide is prepared by Boc-SPPS (non-nucleophilic stratagem) or Fmoc- or Nsc-SPPS (nucleophilic stratagem). The method may be employed to make generators for the production of sterically hindered and non-hindered thioesters and selenoesters according to the invention.

For the non-nucleophilic approach, a preferred method is exemplified below in Scheme 1 for forming the amino acid synthon structure (5): nyl ester). In another method, a preformed activated ester of an amino acid thioester or selenoester (denoted $PG_1$-NH—CH($R_1$)—($CH_2$)$_{n1}$—C(O)—X-Osu) is coupled directly to $R_3$-$L_1$-Support. Preferably, the activated ester of the amino acid thioester or selenoester is sterically hindered. As depicted, $R_1$ is a side chain that may be protected, depending on the side chain, with a group that is removable under non-nucleophilic conditions orthogonal to $PG_1$, and where $n_1$ is from 0 to 2. As can be appreciated, dipeptides or larger peptides can be utilized for the process as well. Also, the first amino acid chosen for bearing the thioester or selenoester component will typically be selected based on the target molecule that one wishes to construct. For example, where a peptide is the target molecule, and the amino acid sequence of the desired peptide is $NH_2$-Gly-Gly-Ser-thioester-polymer, then a $PG_1$-protected serine is the first amino acid coupled to the polymer-modified support.

Scheme 1

$L_1$—Support $R_3$ (direct attachment or on-resin stepwise chain assembly)

$R_3$—$L_1$—Support acyl-X—OSu acyl-X—$R_3$—$L_1$—Support

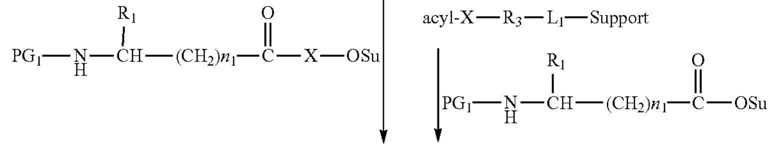

$PG_1$—NH—CH($R_1$)—($CH_2$)$n_1$—C(=O)—X—$R_3$—$L_1$—Support (5)

As shown in Scheme 1, water-soluble group $R_3$ is attached to a linker-functionalized support to generate $R_3$-$L_1$-Support, where $R_3$, $L_1$ and Support are as described above for the structures (3) and (4). An amino acid synthon is coupled to the water-soluble polymer via one of two approaches. In one method, an activated acylthioester or acylselenoester (denoted acyl-X-OSu) is coupled first, wherein the $R_3$-$L_1$-Support is coupled to the sulfur or selenium, as denoted by X. This is followed by removal of the acyl moiety (e.g., piperdine cocktail containing a thiol or selenol reducing reagent), and coupling of an activated amino acid that has its N-terminal alpha amino group protected with a protecting group $PG_1$ that is removable under non-nucleophilic conditions (e.g., a Boc group), where X is sulfur or selenium, and where OSu represents an activated ester moiety (e.g., an OPfp pentafluorophe- The amino acid synthon may also be attached to a support through the alpha-nitrogen or the side chain of the structure (5) through either $L_2$-Support or $L_3$-Support, respectively, as described above. In this situation, on-resin thioesterfication or selenoesterfication reactions analogous to those described below for the nucleophilic approaches may be employed except that the thioester or selenoester may be attached before, during or after a target molecule of interest is synthesized, since nucleophiles can be excluded from the reaction. However, the above method depicted in Scheme 1 is preferred.

The structure (5) may be cleaved to generate a water-soluble thioester or selenoester suitable for solution syntheses, or further elaborated as shown in Scheme 2 below to form the structures (6) and (7), where $PG_1$, R, $R_1$, $R_2$, $R_3$, X, $n_1$, $n_2$, $n_3$, $n_4$, $L_1$ and Support are the same as described above for the structures (3), (4) and (5) above.

Scheme 2

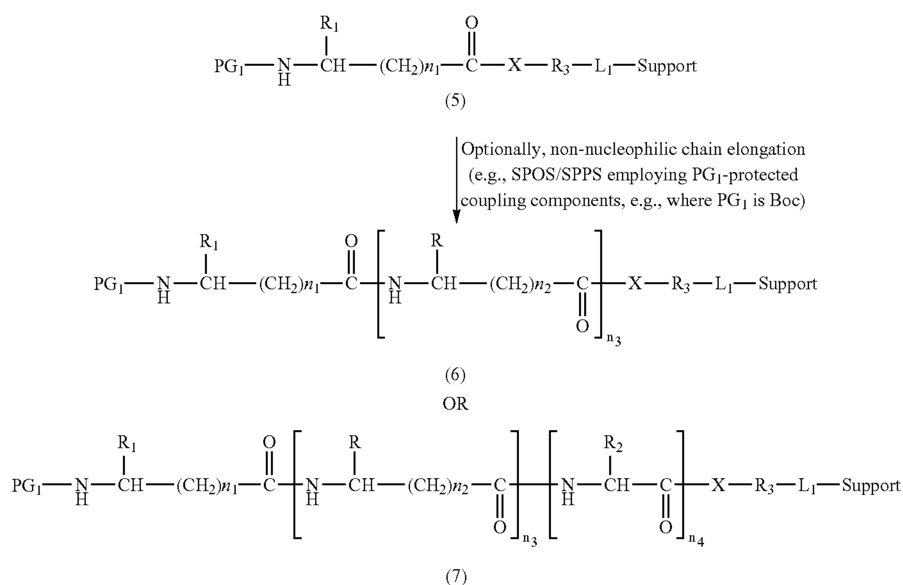

The structures (5), (6) and (7) represent preferred embodiments of the structures (3) and (4) described above, and can be elaborated further or cleaved to form a thioester or selenoester compound of the invention.

For the nucleophilic approach, thioesterfication or selenoesterfication reactions, that are analogous to those described above, are employed except that the thioester or selenoester is attached only after the last nucleophile-based manipulation has been performed. This is necessary as nucleophiles can destroy the thioester or selenoester component prematurely. A preferred embodiment of the non-nucleophilic approach is exemplified below in Schemes 3A, 3B and 3C, which initially employ the compositions of the structures (8) and (9).

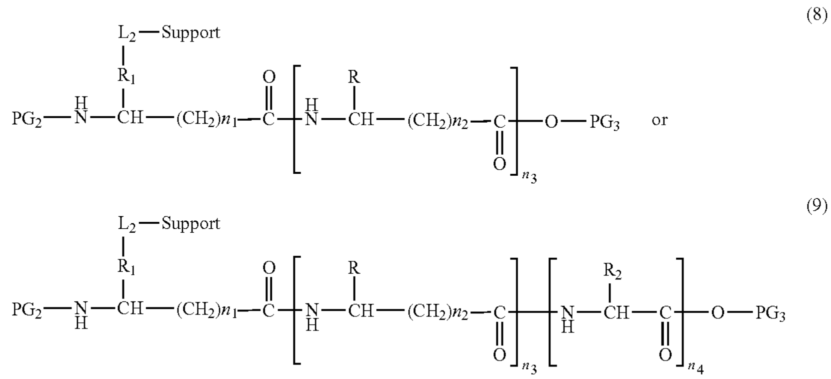

Referring to structures (8) and (9), $PG_2$ is a nucleophile-labile protecting group; Y is a target molecule of interest that may be present or absent; $L_2$ is a nucleophile-stable linker; $R_1$ is a divalent radical lacking reactive functional groups; each R and $R_2$ individually is hydrogen or any organic side chain lacking reactive functional groups; $n_1$ and $n_2$ each are from 0 to 2; $n_3$ is from 0 to 20; $n_4$ is 0 to 1; $PG_3$ is any protecting group that is removable under conditions orthogonal to removal of $PG_2$ and cleavage of $L_2$; and Support is a solid phase, matrix or surface.

As described above, the preferred support is compatible with solid phase organic synthesis (SPOS) or solid phase peptide synthesis (SPPS). The preferred nucleophile-stable linkers are removable under acidic conditions as provided by trifluoroacetic acid (TFA) or anhydrous hydrogen fluoride (HF), under catalytic conditions in the presence of $H_2$, or by other mechanism such as light (e.g., UV photolysis). The amino acid synthon will preferably be composed of an amino acid having a side chain anchored to the support through the linker, and may be provided in the initial composition as a single amino acid residue, peptide, or an organic composition containing an amino acid component, peptide or residue thereof. As also noted above, the organic backbone is lacking reactive functional groups. In most instances, protecting groups, if present on the organic backbone, are preferably selected so as to be removable under the same conditions as the linker. However, protecting groups can be selected that provide an additional level of orthogonality when site-specific modifications to the organic backbone are desired during or after synthesis. Components that bear functional groups that are substantially unreactive under the synthesis conditions may also be unprotected, thus rendering the organic backbone as one lacking reactive functional groups.

The $R_1$ group includes a radical based on an amino acid side chain or derivative thereof that has a functionality capable of covalently binding to the linker $L_2$. For example, preferred $R_1$ groups comprise a side chain of an amino acid selected from aspartic acid, glutamic acid, glutamine, lysine, serine, threonine, arginine, cysteine, histidine, tryptophan, tyrosine and asparagine.

much weaker nucleophile compared to hydrazine. This difference in stability provides the appropriate level of orthogonality.

Compositions of the structures (8) and (9) are easily extensible using conventional Fmoc-based or Nsc-based solid phase organic or peptide synthesis (i.e., SPOS or SPPS) techniques, and provide for a "side chain"-based anchoring during synthesis for elaborating a target molecule of interest Y. For instance, structures (8) and (9) can be employed in a variety of nucleophile-based chain elongation synthesis schemes involving repeated cycles of nucleophilic deprotection and coupling with incoming compounds bearing a reactive moiety and $PG_2$, as illustrated below for structure (8) in Scheme 3A.

Scheme 3A

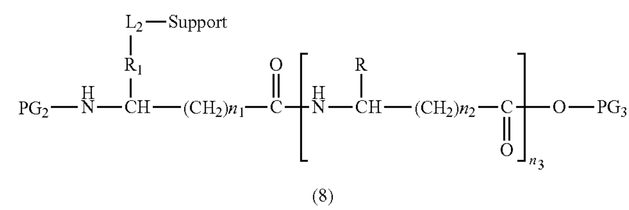

(8)

Nucleophile-based chain elongation and elaboration of Y (e.g., SPOS/SPPS employing $PG_2$-protected coupling components)

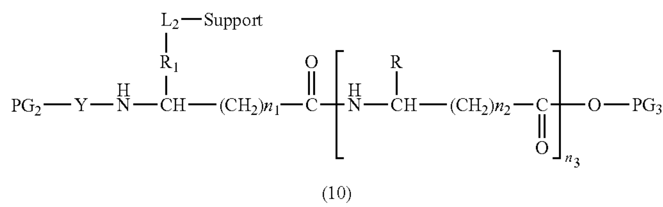

(10)

The protecting group $PG_2$ may comprise any of a variety of nucleophile-labile protecting groups. As noted above, the particular protecting group $PG_2$ may be selected based oh the particular molecule of interest or target molecule, compatibility with other protecting groups or functionalities that will be present during synthesis, or other considerations. The protecting group $PG_3$ may comprise any group capable of protecting a carboxyl group and is orthogonal to the nucleophile-labile protecting group $PG_2$ and the nucleophile-stable linker L, as discussed above. Exemplary protecting groups $PG_3$ and $PG_2$ fitting these criteria include allyl and ODmab groups for the C-terminal carboxyl protection, Fmoc and Nsc when the N-terminal group is an amine, and where a suitable linker would be one cleavable under acidic conditions. For instance, allyl groups are stable to nucleophiles, yet are removable by palladium-catalyzed hydrogenation. ODmab groups can be removed with hydrazine, which is a very strong nucleophile, but are stable to typical conditions employed for removal of most other nucleophile-labile protecting groups, such as N-terminal amino protecting groups Fmoc and 2-(4-nitrophenylsulfonyl)ethoxycarbonyl (Nsc). For instance, Fmoc and Nsc groups are readily removed by piperidine, which is a The nucleophile-labile protecting group $PG_2$ is then selectively removed under nucleophilic conditions to reveal a deprotected functional reactive group. For instance, where $PG_2$ is a nucleophile-labile amino protecting group, and the pendant N-terminal group of Y is an amine, $PG_2$ can be Fmoc or Nsc, and removal thereof can be carried out under basic conditions that do not remove $PG_3$. The deprotected N-terminal reactive functional group is then coupled to a compound of interest bearing a single reactive moiety capable of forming a covalent bond therewith. Various compounds can be employed in this step, depending on the intended end use. The compound of interest may include a non-reactive group, which requires no further protection, or can be one that includes one or more reactive functional groups that need protected. In the latter instance, the protecting group is selected to be orthogonal to removal of $PG_3$. For example, in the case of Fmoc-SPPS the compound of interest can be a final Boc-protected amino acid where the $PG_3$ group is allyl or ODmab. The product of this step of the process is illustrated below for structure (10) in Scheme 3B, which generates the structure (11), where $PG_4$ is a protecting group on the compound of interest that may be present of absent, and when present is removable under conditions orthogonal to $PG_3$.

Scheme 3B

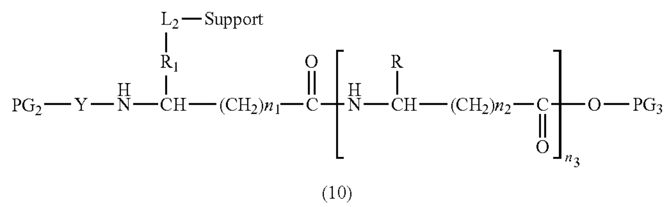

(10)

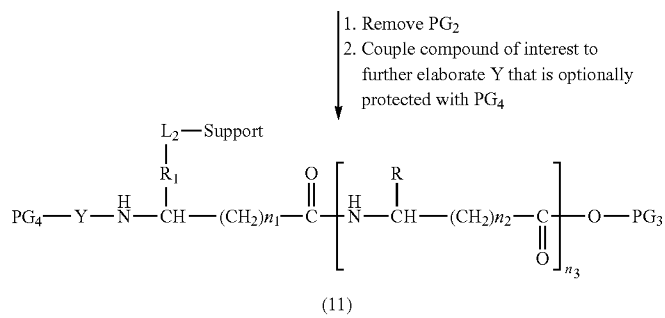

(11)

After coupling of the compound of interest, the C-terminal carboxyl protecting group $PG_3$ is selectively removed to generate a free carboxyl group. Conditions for removing the carboxyl protecting group are chosen based on the protecting group employed. For instance, where an ally group is employed, palladium-catalyzed hydrogenation can be used, or where an ODmab group is employed, the appropriate hydrazine cocktail can be used. The free carboxyl group is then converted to a thioester or selenoester bearing a water-soluble polymer, which is illustrated below in Scheme 3C for structure (11) in the generation of structure (12), where X is sulfur or selenium, and $R_3$ is as described above.

Scheme 3C

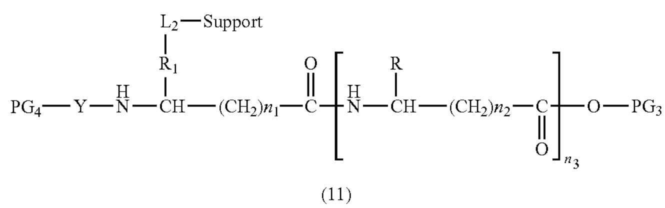

(11)

1. Remove $PG_3$
2. Activate free carboxylate
3. Couple X—$R_3$ to yield acyl-X-ester-polymer

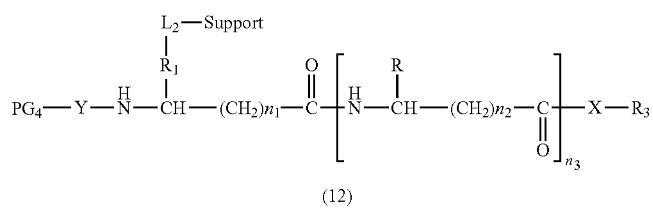

(12)

The structure 12) represents a preferred embodiment of the structures (3) and (4) described above, and the same approach may be applied to generate sterically hindered thioester and selenoester compounds as well. Moreover, the thioester or selenoester compound can be elaborated further on-resin or cleaved to form a thioester or selenoester compound of the invention.

As noted above, preferred side-chains are those provided by an amino acid such as aspartic acid, glutamic acid, glutamine, lysine, serine, threonine, arginine, cysteine, histidine, tryptophan, tyrosine and asparagine, as well as their derivatives and analogs thereof. For example, glutamic acid can be used in a side chain anchoring strategy for generating a target peptide thioester or selenoester via Fmoc-SPPS. In this instance, a single glutamic acid can be used as the precursor where the side chain acid is coupled to an Fmoc-compatible carboxyl-generating linker (e.g., WANG (HMPA), RINK Acid etc.) to a support, an Fmoc group protects the N-alpha amine, and an allyl group protects the O-alpha carboxyl. The desired number of cycles of Fmoc SPPS are carried out as described above, so that a protected peptide is "grown" or otherwise formed in the N- to C-terminal direction from the N-alpha amine of the amino acid joined to the linker, to provide a protected peptide joined or anchored to the linker and support via, the glutamate side chain. The O-alpha carboxyl allyl protecting group can then be removed from the anchored protected peptide under $H_2$/palladium catalyst conditions (e.g., $Pd(Ph_3)_4/PhSiH_3$) in dichloromethane (DCM). Following removal of the allyl protecting group, the 0-alpha carboxyl can then be activated (e.g., using HATU (N-[(dimethylamino)-1H-1,2,3-triazol [4,5-b]pyridiylmethylene]-N-methylmethanaminium hexafluorophosphate N-oxide). The anchored, protected peptide with the activated O-alpha carboxyl can then be reacted with a preformed amino acid thioester-water soluble polymer or salt thereof (e.g., the trifluoroacetic acid (TFA) salt form) to produce a target peptide thioester anchored to the linker and support. In this example, the backbone side chains of the peptide are protected with acid-labile protecting groups. An acid such as TFA may then be used to cleave the linker and release the target peptide thioester-water soluble polymer from the support and remove the acid-labile side chain protecting groups from the target.

Another specific example illustrating the side chain anchoring of an initial amino acid to a support prior to formation of a target water-soluble peptide thioester-polymer is lysine. For example, a support bound WANG linker can be treated with N,N'-disuccinimidyl carbonate (DSC)/4-dimethylaminopyridine (DMAP) in N,N-dimethyl formamide (DMF) to activate the linker for coupling. The activated linker is then treated with the TFA salt of Nα-Fmoc-Oα-allyl lysine, in N,N-diisopropylethylamine (DIEA)/DMF, to form a linker with a urethane group made with the lysine side chain ϵ-amino group. The lysine residue thus anchored by its side chain provides an initial basis for Fmoc-based SPPS synthesis, which can be carried out to generate a peptide by stepwise growth in the N- to C-terminal direction from the N-alpha amine as described above. Once the desired peptide is formed with the desired number of cycles of Fmoc-SPPS, the N-alpha amine can be protected with a nucleophile-stable protecting group such as a Boc-protected amino acid, and then the O-alpha carbonyl deprotected using $H_2$/Pd ($Pd(Ph_3)_4/PhSiH_3$). The free O-alpha carbonyl may then be activated using 7-azabenzotroazol-1-1yloxtris (pyrrolidino) phosphonium hexafluorophosphate (PyAOP) in DIEA/DMF, and reacted with preformed acyl-thioester water-soluble polymer to produce an anchored target peptide thioester. The target peptide thioester can then be cleaved from the support by treatment with TFA cocktails to yield the free target water-soluble peptide thioester-polymer.

The above-described nucleophilic strategy for side-chain anchored amino acid synthons can be applied to backbone anchored amino acid synthons as well. The main difference here is the use of a linker that is attached to the backbone alpha nitrogen of an amino acid synthon for coupling to the support. Several linkers for this approach are well known and can be used (Barany et al., J. Org. Chem. (1999) 64(24):8761-8760; Ishi et al., Biosci. Biotechnol. Biochem. (2002) 66(2):225-232). To improve yields in the backbone approach, care should be taken to avoid aminolysis in the first on-resin coupling reaction, which can occur when the initial coupling employs a single amino acid capable of forming a 5-member or 6-member cyclic side product via aminolysis of the resin-supported amino acid. For example, aminolysis can be avoided by using a dipeptide or larger in the first coupling, and/or using a resin that employs an amino acid synthon comprising a tri-peptide or larger, or a combination thereof.

The organics, equipment, supports, amino acids and diversity components, linkers, and protecting groups finding use in the above-described aspects of the invention can be obtained from a variety of commercial sources, prepared de novo, or a combination thereof. Moreover, the reagents and other materials employed for the method, as well as alternative components will be apparent to one of ordinary skill in the art (See, e.g., "Protecting Groups in Organic Synthesis", 3rd Edition, T. W. Greene and P. G. M. Wuts, Eds., John Wiley & Sons Inc., 1999; NovaBiochem Catalog 2000; "Synthetic Peptides, A User's Guide," G. A. Grant, Ed., W. H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000, and elsewhere).

Utility

The subject water-soluble selenoester and thioester compounds, (and generators thereof in certain embodiments) as described above, are particularly useful in peptide and polypeptide synthesis techniques that employ thioester and/or selenoester-mediated chemical ligation. Such protocols/applications are well known to those of skill in the art, and described in WO 98/56807; WO 02/18417; and WO 02/20557 (the United States Provisional Priority Applications of which are herein incorporated by reference) as well as in U.S. Pat. No. 6,326,468; the disclosure of which is herein incorporated by reference.

Kits

Given the broad range of use, the subject thioester and selenoester generators and compounds also may be provided in kits and the like. As such, also provided are kits for use in the subject invention, where such kits may comprise containers, each with one or more of the various reagents utilized in the methods, including, for example, water soluble polymer functionalized solid supports, blocked and/or activated monomers, activators, deblockers, buffers, solvents and the like The kits may further include instructions for using the kit components in the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

ILLUSTRATIVE EXEMPLARY EMBODIMENTS

The above-described embodiments of the invention will be more fully understood by reference to additional specific examples, compositions and reaction schemes shown below and in the Figures.

Referring now to FIG. 1, the structure of (1A) illustrates a general thioester or selenoester composition of the invention exemplified by a peptide-thioester-polymer, or peptide-selenoester-polymer. In particular, the structure of (1A) depicts a peptide denoted "Peptide" coupled to a water-soluble polymer denoted "Polymer" through an alpha-amino acid thioester or selenoester, where X is sulfur or selenium, and where R is a side chain of an amino acid. FIG. 1 also shows structures (1B) through (1D) that illustrate three different general embodiments in accordance with the invention that include structure (1A) attached to a support resin in different configurations and preferred thioester or selenoester generators for production of the structure (1A). In particular, structure (1C) illustrates a water-soluble compound of structure (1A) anchored to a support via a side-chain linker. Structure (1D) illustrates a water-soluble compound of the structure (1A) anchored to a support via a backbone nitrogen linker system. Structure (1B) illustrates a water-soluble compound of structure (1A) anchored to a support via a linker attached to the water-soluble polymer. In reference to structures (1B) through (1D) of FIG. 1, Peptide, X, Polymer, L and Support are as described above for structure (1A).

Figure 2:
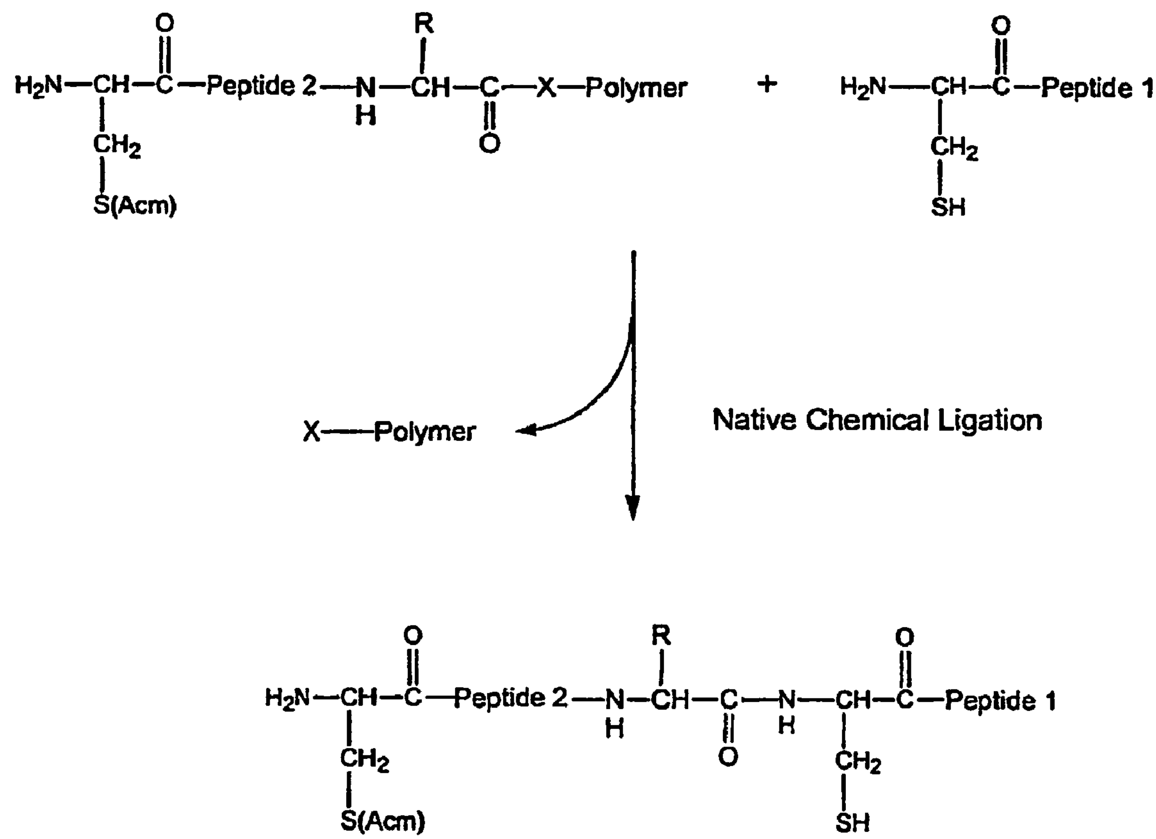
FIG. 2 depicts an exemplary use of a water-soluble thioester or selenol ester compounds of the invention in a method of native chemical ligation.

Referring now to FIG. 2, a water-soluble peptide thioester-polymer or selenoester-polymer (such as in FIG. 1 (1A)) is joined by native chemical ligation to another peptide bearing an unprotected N-terminal cysteine. In this example, the water-soluble peptide thioester-polymer or selenoester-polymer bears an Acm-protected N-terminal cysteine. Ligation of the two peptides forms a native amide bond at the ligation site and displacement of the thioester-polymer or selenoester-polymer component. The Acm of the ligated product may then be removed for additional ligation reactions.

The following specific example illustrates a preferred embodiment in which generator structure (1B) of FIG. 1 is constructed to form a thioester generator of the invention, and utilized to produce a peptide-thioester-polymer embodied in FIG. 1 (1A), in which the polymer component is a water-soluble polyamide polymer of discrete length. In particular, a target molecule of interest comprising the thioester water-soluble polymer of structure (13) can be generated on an amide-generating resin such as a $NH_2$-Leu-PAM-resin, where Y is a target molecule of interest bearing an N-terminal amino group, R' is the side chain of an amino acid or derivative thereof, "i" is from 1 to 2, and where "i" is 1 then $R_7$ and $R_8$ are both hydrogen for a non-sterically hindered thioester, and are, for example, —$CH(CH_3)_2$ and hydrogen, or —$CH_3$ and —$CH_3$, respectively, for a sterically hindered thioester, and "n" is a discrete integer from 2 to 12.

(13)

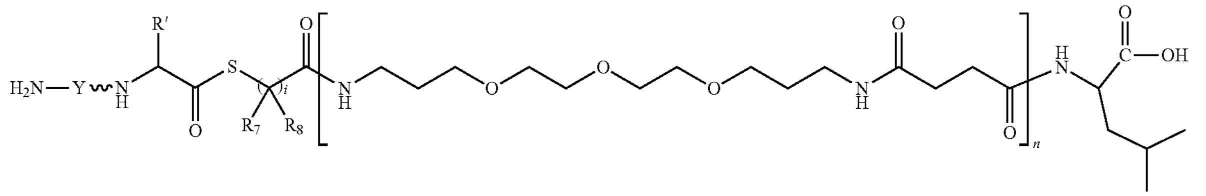

Specifically, structure (13) can be produced by coupling a desired water-soluble polyamide polymer to the $NH_2$-Leu-PAM resin via stepwise chain assembly or by attachment in its full linear form. This process is illustrated below in Schemes 4 and 5 for the stepwise chain assembly of a water-soluble thioester-polymer compound.

Scheme 4

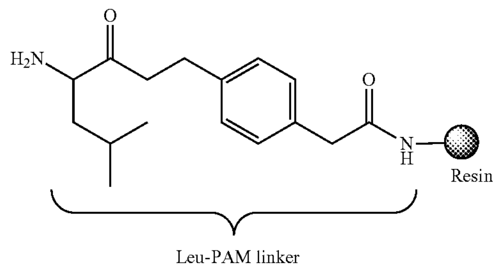

-continued

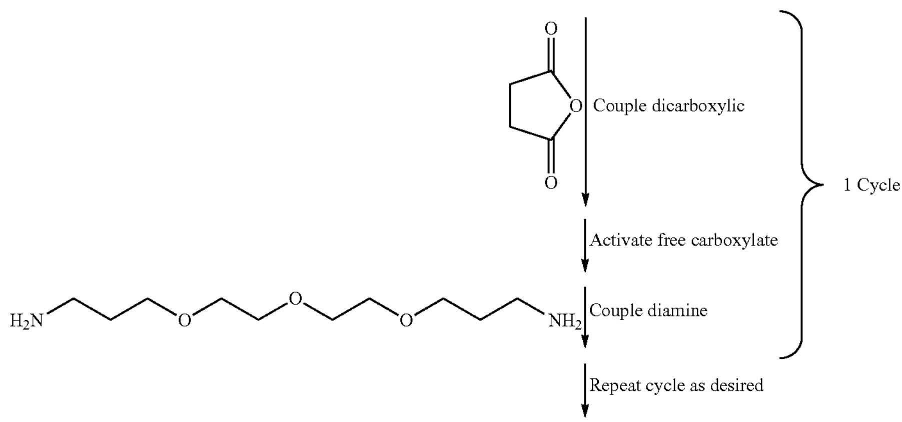

(14)

Structure (14), where n is the number of cycles of polymer synthesis, is then coupled to a preformed acylthioester (15), produced, for example, as the OPfp ester as follows:

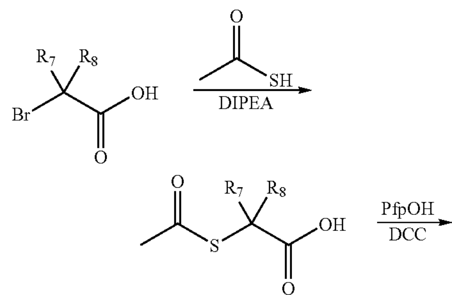

-continued

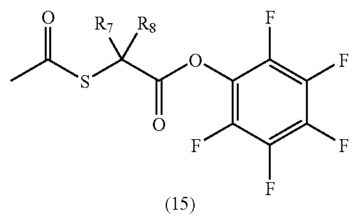

(15)

The acyl of resulting a cylthioester composition (16) may then be removed, e.g., piperdine cocktail containing β-mercaptoethanol, which is then suitable for coupling the active ester of an initial amino acid or other compound, such as an initial Boc-protected amino acid as shown in the structure (17), followed by Boc-SPPS to generate a resin-bound target molecule of interest, as shown in structure (18). Cleavage of (18) in HF yields compound. (13).

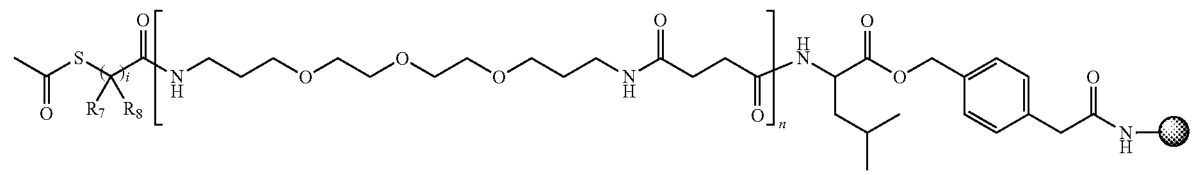

(16)

1. Remove Acyl, if required
2. Couple Boc-aa

-continued

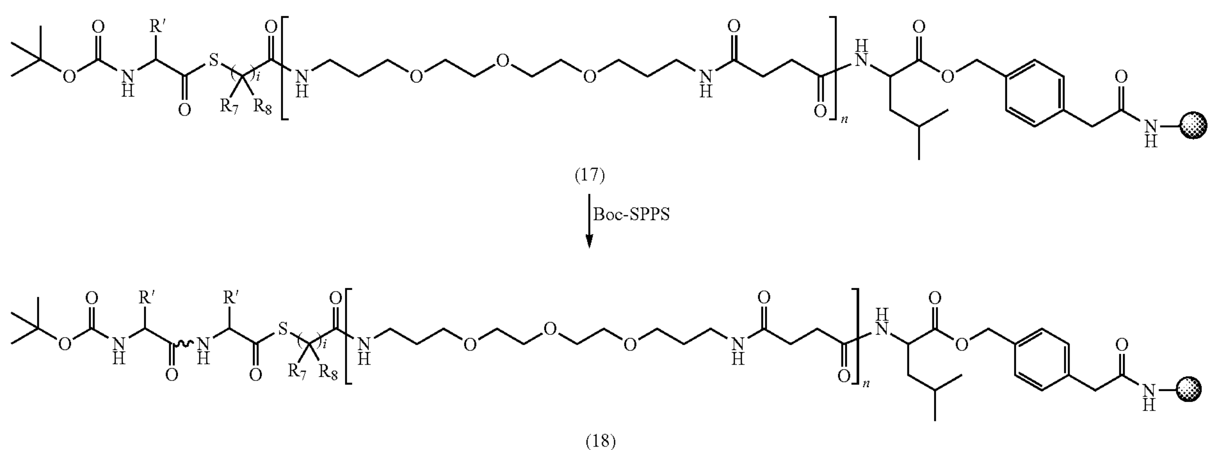

Where the last coupled amino acid of structure (18) prior to cleavage is an Acm-protected cysteine, the structure (19) can be produced. Where an internal amino acid contains an orthogonally protected side-chain group, e.g., Fmoc-protected side chain of lysine (K), and/or post-elongation modifications that form an unprotected side-chain functional group that is substantially unreactive under cleavage conditions, e.g., aminooxy-functionalized side chain of lysine, various combinations of the structure (20) can be produced.

(19)

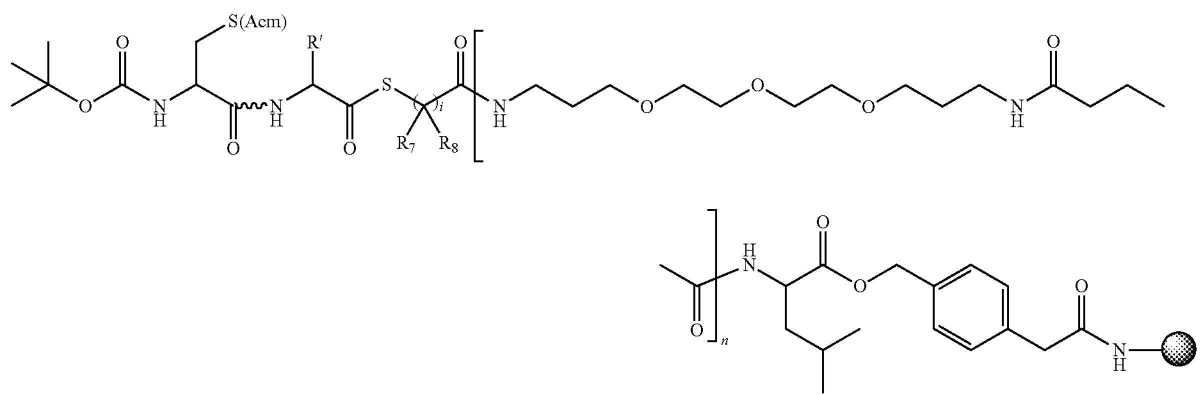

(20)

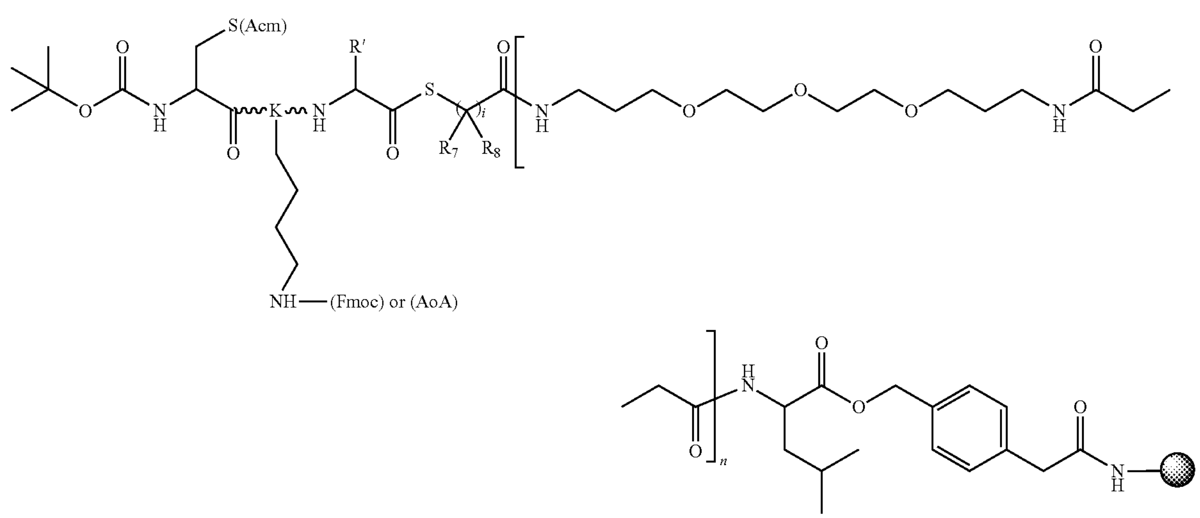

The above structures (18), (19) and (20) are but a few of a variety of representative examples illustrating the flexibility of the invention and the broad ranges of use of the subject thioester and selenoester generators and compounds of the invention.

All publications and patent applications mentioned in this specification are herein incorporated by reference to the same extent as if each individual publication or patent application was specifically and individually indicated to be incorporated by reference.

Having now generally described the invention, the same will be more readily understood through reference to the additional following examples, which are provided by way of illustration, and are not intended to be limiting of the present invention, unless specified.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for. Unless indicated otherwise, parts are parts by weight, molecular weight is weight average molecular weight, temperature is in degrees Centigrade, and pressure is at or near atmospheric.

The following experimental examples provide for the synthesis of certain peptides using tert-butyloxycarbonyl- (Boc)-compatible synthesis, including Boc-based solid-phase peptide synthesis (SPPS). Those skilled in the art will recognize, however, that the water-soluble thioester and selenoester generators and related methods of the invention may be applied in 9-fluorenylmethoxycarbonyl-(Fmoc)-compatible synthesis, including Fmoc-based SPPS, as well as combinations of Fmoc- and Boc-compatible synthesis. Additional embodiments include 2-(4-nitrophenylsulfonyl)ethoxycarbonyl (Nsc), allyloxycarbonyl (Alloc), and other protection schemes compatible with SPPS and nucleophile-labile thioesters and selenoesters. The experimental examples also utilize peptide synthesis involving chain extension from an N-terminus. Those skilled in the art will recognize that peptide synthesis involving extension from the C-terminus may also be carried out using the invention. Thus, it should be understood that the invention is not limited to the particular embodiments described below, as variations of these embodiments may be made and still fall within the scope of the appended claims.

Moreover, the following experimental examples provide a detailed description of the Boc-based solid phase synthesis of certain specific peptide thioester compounds. Those skilled in the art will recognize that the same or similar procedures described below may be used to synthesize numerous types of thioester and thioester compounds and generators thereof. The selenium based-chemistry associated with selenoester formation is well known in the art and, where appropriate, may be substituted. Table 1 provides a list or glossary of abbreviations used in the following experimental examples.

TABLE 1

| | |
|---|---|
| Acm | acetamidomethyl |
| Alloc | allyoxycarbonyl |
| BOP | benzotriazol-1-yloxytris(dimethylamino)phosphonium hexafluorophosphate |
| Br,Cl Z | Br,Cl Benzylcarbamate |
| DCM | dichloromethane |
| DDE | 4,4-dimethyl-2,6-dioxocycloex 1-ylidene |
| DIPCDI | N,N-diisopropylcarbodiimide |
| DIPEA | N,N-diisopropylethylamine |
| DMAP | 4-dimethylaminopyridine |
| DMF | N,N-dimethylformamide |
| DMSO | dimethylsulfoxide |
| EtOH | ethanol |
| Fmoc | 9-fluorenylmethoxycarbonyl |
| FM | 9-Fluorenylmethyl |
| HATU | (N-[(dimethylamino)-1H-1,2,3-triazol[4,5-b]pyridiylmethylene]-N-methylmethanaminium hexafluorophosphate N-oxide). |
| HBTU | N-[(1-H-benzotriazol-1-yl)(dimethylamine)methylene]-N-methylmethanaminium hexafluorophosphate N-oxide previously named 0-(benzotriazol-1-yl)-1,1,3,3-tetramethyluronium hexafluorophosphate |
| HF | hydrofluoric acid |
| HMP resin | 4-hydroxymethylphenoxy resin; palkoxybenzyl alcohol resin; or Wang resin |
| HOAt | 1-hydroxy-7-azabenzotriazole |
| HOBt | 1-hydroxybenzotriazole |
| IP10 | Interferon-gamma inducible protein 10 kDa |
| Mbh | dimethoxybenzhydryl |
| MBHA resin | 4-methylbenzhydrylamine resin |
| Meb | p-MethylBenzyl |
| MMA | N-methylmercaptoacetamide |
| Mmt | p-Methoxytriityl |
| Mob | p-MethoxyBenzyl |
| Msc | 2-Methylsulfoethylcarbamate |
| Msz | 4-Methylsulfinylbenzylcarbamate |
| Mtr | 4-methoxy-2,3,6-trimethylbenzene sulfonyl |
| NMM | Nmethylmorpholine |
| NMP | N-methylprrolidone,N-methyl-2-pyrrolidone |
| Nsc | 4-nitrophenylethylsulfonyl-ethyloxycarbonyl |
| OPfp | pentafluorophenyl ester |
| OtBu | tert-butyl ester |
| PAC | peptide acid linker |
| PAL | peptide amide linker |
| Pbf | 2,2,4,6,7-pentamethyldihydrobenzofuran-5-sulfonyl |
| PEG-PS | polyethylene glycol-polystyrene |
| Picolyl | methyl-pyridyl |
| Pmc | 2,2,4,6,8-pentamethylchroman-6-sulfonyl |
| PyAOP | 7-azabenzotroazol-1-1yloxtris(pyrrolidino)phosphonium hexafluorophosphate |
| S-tBu | tert-butyl-thio |
| Tacam | Trimethylacetamidomethyl |
| tBoc | tert-butyloxycarbonyl |
| TBTU | 0-(benzotriazol-1-yl)-1,1,3,3-tetramethyl uronium tetrafluoroborate |
| tBu | tert-butyl |
| TFA | trifluoroacetic acid |
| Tis | Trisisopropylsilane |
| Tmob | 2,4,6-trimehoxybenzyl |
| TMOF | trimethylorthoformate |
| Troc | 2,2,2Trichloroethylcarbamate |
| Trt | triphenylmethyl |

Example 1

General Materials and Methods

Peptide Synthesis

Water-soluble thioester peptides are synthesized on a thioester-generating resin described in Example 2, whereas standard peptide thioesters are synthesized on a standard thioester generating resin (Hackeng, et al., PNAS (1999) 96:10068-10073). Both the water-soluble and standard thioester peptides are synthesized following the in situ neutralization protocol for Boc (tertbutoxycarbonyl) chemistry and stepwise solid phase peptide synthesis (SPPS) using established SPPS, side-chain protection and thioester-resin strategies (Hackeng, et al., PNAS (1999) 96:10068-10073;

and Schnolzer, et al., Int. J. Pept. Prot. Res., (1992) 40:180-193)) on an AB1433A automated peptide synthesizer or by manual chain assembly, or ordered and acquired from commercial vendors. For instance, a standard set of Boc SPPS protecting groups are used, namely: Arg(Tos); Asp(cHex); Cys(4MeBzl) & Cys(Acm); Glu(cHex); His(DNP); Lys (CIZ); Ser(Bzl); Thr(Bzl); Trp(formyl); Tyr(BrZ); Met, Asn, Gln are side-chain unprotected. Non-thioester peptides are synthesized on a —O—$CH_2$—PAM-resin. Peptides are deprotected and simultaneously cleaved from the resin support using HF/p-cresol according to standard Boc chemistry procedure. The peptides are purified by preparative C4 reversed-phase-high pressure liquid chromatography (RP-HPLC). Fractions containing pure peptide are identified using ES-MS (electrospray ionization mass spectrometry), pooled and lyophilized for subsequent ligation. For peptides containing protecting groups not removed in HF/p-cresol, the protecting groups are retained, for instance, such as Acm-protected cysteines, and DNP-protected histidines.

Acm and DNP Protecting Group Removal

DNP-removal from histidines occurs under the nucleophilic conditions employed for native chemical ligation. For Acm-protected peptides, Acm-removal is performed following standard mercury-acetic acid conditions by dissolving the peptide in TFE at a concentration of 10-70 mg/ml. Alternatively, the reaction is performed in HPLC buffer. The solution is diluted with 4M freshly prepared urea, for a final concentration of peptide of 4 mg/ml and TFE of 20%. A threefold molar excess (relative to the total expected cysteine concentration) of a 30 mg/ml $Hg(acetate)_2$ solution in 3% aqueous acetic acid is added and the solution is stirred for one hour. The solution is then made 20% in β-mercaptoethanol, and 60% 100 mM acetate, pH4 containing 6M guanidinium chloride. The solution is loaded onto C4 coated reversed-phase beads and desalted by washing with low organic buffer (15% aqueous isopropanol, 0.1% TFA) followed by elution with high-organic buffer (90% aqueous isopropanol, 0.1% TFA). Fractions containing the desired product are identified by ES-MS and pooled and lyophilized.

Native Chemical Ligation

Native chemical ligation is carried out by admixing a first peptide bearing an N-terminal cysteine with a 1.5 fold excess of a second peptide (the peptide-thioester segment), and dissolved in 200 mM phosphate buffer (pH 7.9) containing 6 M guanidinium chloride at a concentration of 24 mM concentration and 1% thiophenol is added. After ligation, 1 equivalent (eq) v/v TFE (trifluoroethanol), 2 eq v/v 6M guanidinium chloride, 100 mM Tris-HCl, pH 8.5 and 1 v/v β-mercaptoethanol is added to the ligation mix and incubated for 30 minutes. The solution is acidified with a solution of 15 mg/ml TCEP (tris(2-carboxyethyl)phosphine.HCl) in glacial acetic acid and loaded onto a preparative C4 reversed-phase HPLC column (1 inch diameter). The peptides are then purified by preparative gradient reversed-phase HPLC. Fractions containing the desired ligated product are identified by ES-MS and pooled.

Example 2

Synthesis of Water-Soluble Polymer Thioester-Generating Resin

The following Boc-protected amino acid ($aa_x$)-thioester water-soluble polymer generating resin shown below is prepared for synthesis of water-soluble peptide thioesters:

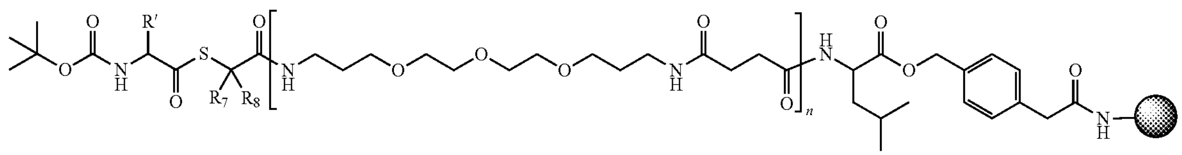

where R' is the side chain of the first amino acid for the Boc-SPPS of a target peptide, $R_7$ and $R_8$ are each individually hydrogen, —$CH_3$, or —$CH(CH_3)_2$, and where n is a discrete integer from 2 to 12.

On a 0.5 mM scale 400 mg succinic anhydride is dissolved in 8 ml of 0.5M HOBT (N-hydroxybenzotriazole) containing 400 ul DIEA is coupled to $NH_2$-Leu-PAM-resin (substitution ~0.5 mmol/g) for 10 minutes. The resin is activated with 8 ml of fresh 1 M CDI (Carboxydiimidazole) solution in DMF and 4 mL (4,7,10)-trioxatridecane-1,13diamine (TTD) is added in 4 mL 0.5M HOBT solution coupled for 30 minutes. After n cycles of this process, and depending on the target peptide sequence, different starting resins are constructed to provide the first amino acid for Boc-SPPS in the target sequence by one of two protocols.

In one protocol, a selected carboxylic acid, such as acylmercaptoacetic acid, is activated in DCC (1,3-dicyclohexylcarboiimide) with PfpOH (pentafluorophenyl ester) to give S-Acetylthioglycolic acid pentafluerophenyl ester (SAMA-Opfp) and coupled to the resin following standard DCC/PfpOH activation and coupling protocols (e.g., "Fmoc Solid Phase Peptide Synthesis, A Practical Approach," Eds., W. C. Chang and P. D. White, Oxford University Press, 2000). This is followed by removal of the acyl moiety by a piperdine cocktail containing a thiol or selenol, such as piperdine and β-mercaptoethanol in DMF, and then followed by coupling of a selected Boc-protected amino acid (typically 2.5 mmole) dissolved and activated in 4.75 ml 0.5 M (2.375 mmole) HBTU in DMF containing 150 microliter (111 mg, 0.825 mmole) DIEA, typically for 1 hour with vortex agitation, followed by draining.

In a second protocol, a selected preformed Boc-amino acid thioester (e.g., Boc-protected amino acid containing a thioester) (typically 0.5 mmol) is suspended in DCM (1 mL) and DIEA (1.5 mmol) added. The solution is vortexed at room temperature for 2 min and added to the resin. Solid HATU (0.5 mmol) is then added directly to the resin-mixture, mixed and stirred occasionally for 30 min.

For both protocols, the resin is then drained, and washed with DCM, DMF, DCM, and then dried in vacuo for 1 h to constant weight.

Example 3

Synthesis of Peptide-GRFN 1712

Peptides GRFN-1712 and GRFN-1712-$PLP_3$ having the sequences depicted below are synthesized in accordance with Example 1 on a 0.15 mmol scale using HBTU coupling chemistry and Boc-SPPS. For GRFN-1712-$PLP_3$-Leu the following Boc-tryptophan(formyl)-thioester-$PLP_3$ generating resin is used:

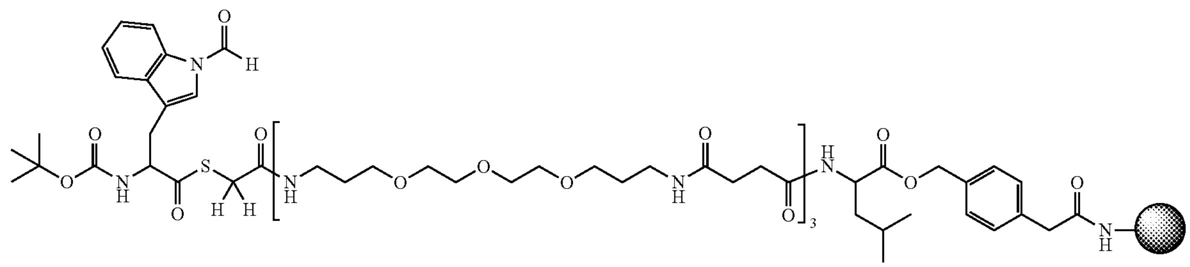

Amino acids free of ethyl acetate are used as precursor materials. The resulting peptide-thioesters are deprotected and simultaneously cleaved free of the supporting resin and linker in HF/p-cresol (9 to 1 ratio) at 0° C. for one hour.

```
GRFN-1712                                  (SEQ ID NO: 1)
CSLNE KITVP DTKVN FYAWK RMEVG QQAVE VWQGL
ALLSE AVLRG QALLV KSSQP W-thioester (where Cys1 is
Acm protected)
```

-continued

```
GRFN 1712-PLP3                             (SEQ ID NO: 2)
CSLNE KITVP DTKVN FYAWK RMEVG QQAVE VWQGL
ALLSE AVLRG QALLV KSSQP W-thioester-PLP3-L (where
Cys1 is Acm protected)
```

Example 4

Handling Properties of Peptide-GRFN1712

The deprotected and cleaved GRFN 1712-thioester-$PLP_3$-Leu prepared in accordance with Example 3 is completely dissolved in 50% aqueous acetonitrile containing 0.08% trifluoroacetic acid (TFA). Analysis of the crude cleavage product for the 1712-thioester-$PLP_3$ by HPLC and Electrospray Mass Spectroscopy (ES-MS) shows it to be the major product, including a very sharp and predominant peak by HPLC analysis for the desired product. In comparison, the standard 1712 peptide-thioester (i.e., without the water-soluble polymer) prepared in accordance with Example 3 requires TFE and TFA for dissolution; also, HPLC and ES-MS analyses showed a complex heterogenous crude cleavage product.

Relative solubility of the 1712-$PLP_3$-Leu thioester and the standard 1712 thioester also are tested in 50% ACN/$H_2O$. The 1712-$PLP_3$-Leu thioester (10 mg/mL) is completely dissolved, whereas the standard 1712 thioester is only partially soluble at low concentration.

Example 5

Synthesis of Peptide-GRFN 1852-$PLP_3$-Leu

The following thioester peptides having the amino acid sequences shown below are synthesized in accordance with Example 1 on a 0.15 mmol scale using HBTU coupling chemistry and Boc-SPPS. For GRFN 1852-$PLP_3$-Leu, the following Boc-leucine-thioester-$PLP_3$-Leu generating resin is used:

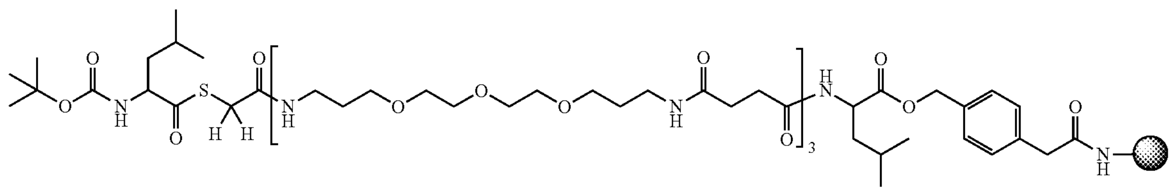

Amino acids free of ethyl acetate are used as precursor materials. The resulting peptide-thioesters are deprotected and simultaneously cleaved free of the supporting resin and linker in HF/p-cresol (9 to 1 ratio) at 0° C. for one hour.

```
GRFN 1852                                  (SEQ ID NO: 3)
CLSQL HSGLF LYQGL LQALE GISPE LGPTL DTLQL DVADF
ATTIW QQMEE L-thioester (where Cys1 is Acm
protected)

GRFN 1852-PLP3                             (SEQ ID NO: 4)
CLSQL HSGLF LYQGL LQALE GISPE LGPTL DTLQL DVADF
ATTIW QQMEE L-thioester-PLP3-Leu (where Cys1 is
Acm protected)
```

Example 6

Handling Properties of Peptide-GRFN 1852

Figure 3A:
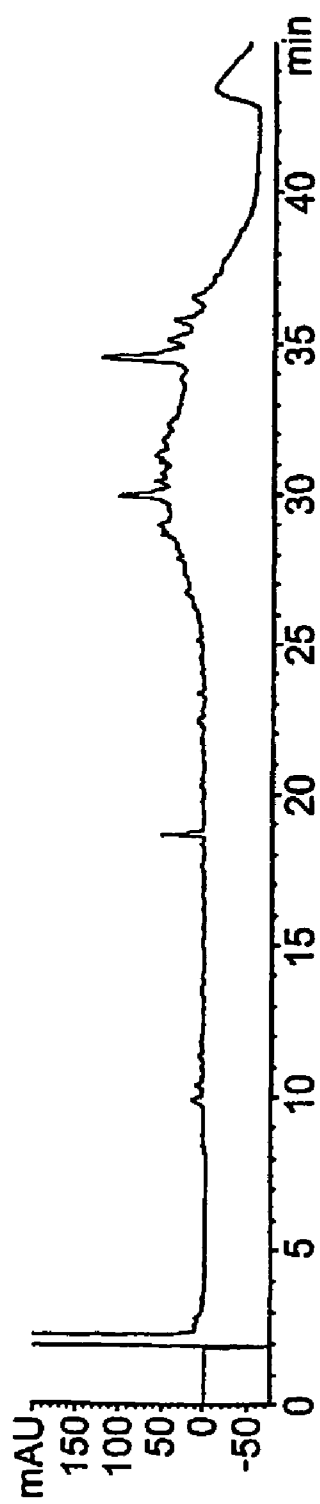
FIGS. 3A-3B depict a Reversed-Phase High Performance Liquid Chromatography (HPLC) chromatogram illustrating purities of a crude cleavage product containing an exemplary peptide-thioester devoid of a water-soluble polymer (FIG. 3A), compared the same peptide-thioester that includes a water soluble polymer (FIG. 3B).
Figure 3B:
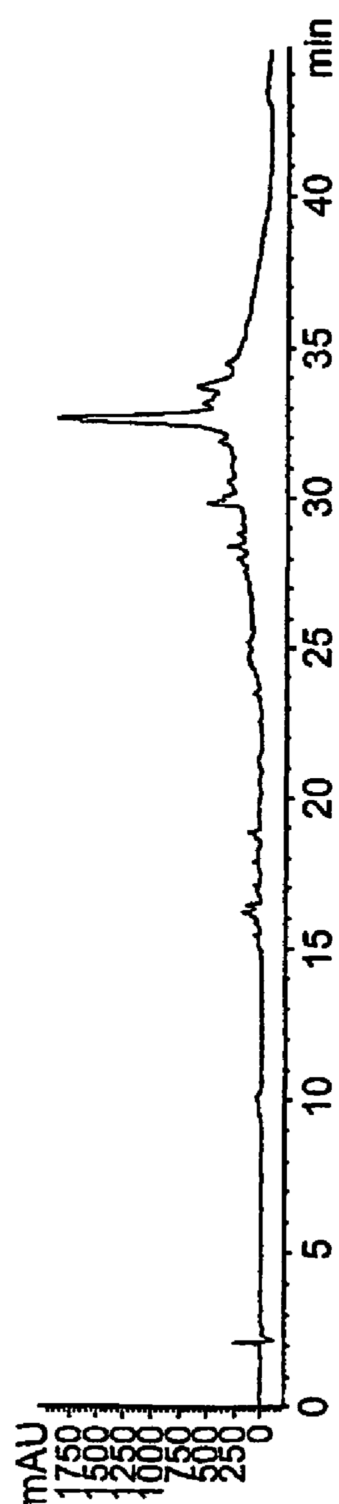

As with GRFN peptide 1712, the deprotected and cleaved GRFN 1852-$PLP_3$-Leu containing a thioester is completely dissolved in 50% aqueous acetonitrile containing 0.08% trifluoroacetic acid (TFA). In contrast, the non-polymer modified peptide GRFN 1852 is poorly soluble. In addition, when comparing the purity of the crude GRFN 1852-PLP$_3$ thioester cleavage product as compared to that of the standard GRFN 1852 (i.e., without the water-soluble polymer) by ES-MS or HPLC, the water-soluble polymer thioester peptide is clearly better (See, e.g., the HPLC chromatogram illustrated in FIGS. 3A-3B). As illustrated in FIG. 3B, the major peak is the target product.

The above results and discussion demonstrate that the subject methods provides improved methods of SPPS, particularly in the SPPS generation of thioester and selenoester compounds, where advantages of the invention include improved solubility and/or reduced aggregation of crude peptide products, leading to better purification, higher yield, and other advantages. As such, the subject methods represent a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A water-soluble thioester or selenoester compound of the formula:

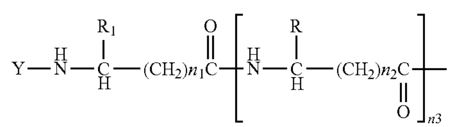

$$—X—C(R_7)(R_8)—U—\text{Polymer}$$

wherein Y is selected from the group consisting of: an amino acid, a peptide, and a polypeptide;

X is sulfur or selenium;

$n_1$ and $n_2$ are each from 0 to 2, and $n_3$ is from 0 to 100;

R and $R_1$ are individually selected from the group consisting of: hydrogen, a side chain of an amino acid, a branched alkane, a cycloalkane, an alkyl-substituted aryl or heteroaryl group, and combinations thereof;

$R_7$ and $R_8$ are each, individually, selected from hydrogen, substituted and unsubstituted linear or branched chain alkyl, aryl, heteroaryl and benzyl;

U is a linker or spacer and may be present or absent and, when present, consists of a linear or branched chain alkyl or heteroalkyl group of up to 18 carbon atoms;

Polymer is a water-soluble polymer of a formula selected from the group consisting of: —[C(O)-ϕ-C(O)—NH-ψ-NH]$n_5$ and —[NH-ψ-NH—C(O)-ϕ-C(O)]$n_5$, where $n_5$ is an integer from 2 to 100, and ϕ and ψ are divalent radicals that may be the same or different and are selected from the group consisting of —(($CH_2$)$n_6$-($CH_2CH_2O$)$n_7$-($CH_2$)$n_6$-)- and —(($CH_2$)$n_6$-(O—$CH_2$—$CH_2$)$n_7$-($CH_2$)$n_6$-)-, where $n_6$ is an integer from 1 to 6 and $n_7$ is an integer from 2-50, and where ϕ can also be —($CH_2$—$CH_2$)— and ψ can also be —($CH_2$—($CH_2$—$CH_2$—O)$_3$—$CH_2$—$CH_2$—$CH_2$)— or —($CH_2$—$CH_2$—$CH_2$—(O—$CH_2$—$CH_2$)$_3$—$CH_2$)—.

2. The thioester or selenoester compound according to claim 1 wherein Y is a peptide or polypeptide.

3. The thioester or selenoester compound according to claim 2 wherein said peptide or polypeptide comprises protected amino acids.

4. The thioester or selenoester compound according to claim 2 wherein said Y contains an N-terminal amino acid containing a group that supports chemical ligation.

5. The thioester or selenoester compound according to claim 1 wherein $R_3$ comprises a group of the formula —C($R_7$)($R_8$)-U-Polymer, where $R_7$ and $R_8$ are each individually selected from the group consisting of: hydrogen or linear, branched, substituted, or unsubstituted alkyl, aryl, heteroaryl, and benzyl, and U is selected from the group consisting of alkyl, aryl, heteroalkyl, heteroaryl, alkoxy, of up to 18 carbon atoms, and Polymer is selected from the group consisting of: —[C(O)-ϕ-C(O)—NH-ψ-NH]$n_5$ and —[NH-ψ-NH—C(O)-ϕ-C(O)]$n_5$, where $n_5$ is an integer from 1 to 100, and ϕ and ψ are divalent radicals selected from the group consisting of —(($CH_2$)$n_6$-($CH_2CH_2O$)$n_7$-($CH_2$)$n_6$-)- and —(($CH_2$)$n_6$-(O—$CH_2$—$CH_2$)$n_7$-($CH_2$)$n_6$-)-, where $n_6$ is an integer from 1 to 6 and $n_7$ is an integer from 2-50.

6. The thioester or selenoester compound of claim 1 wherein Polymer comprises a divalent radical of having the structure:

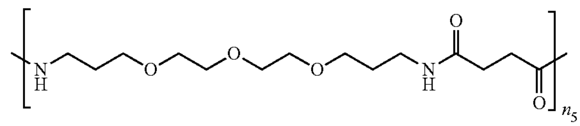

where $n_5$ is an integer of from 2 to 12.

7. The thioester or selenoester compound of claim 5 wherein

ϕ is —($CH_2$—$CH_2$)— and ψ is —($CH_2$—($CH_2$—$CH_2$—O)$_3$—$CH_2$—$CH_2$—$CH_2$)— or —($CH_2$—$CH_2$—$CH_2$—(O—$CH_2$—$CH_2$)$_3$—$CH_2$)—.

8. The thioester or selenoester compound of claim 1 wherein R is a group of the structure —C($R_4$)($R_5$)($R_6$), where $R_4$, $R_5$, and $R_6$ each individually are selected from the group consisting of: hydrogen, linear, branched, substituted or unsubstituted alkyl, aryl, heteroaryl, and benzyl.

9. The thioester or selenoester compound of claim 5 wherein

Y is a peptide or polypeptide;

X is sulfur;

$n_1$ and $n_2$ are 0;

$R_7$ and $R_8$ are each individually selected from the group consisting of: hydrogen, —$CH_3$, and —CH($CH_3$)$_2$.

10. The thioester or selenoester compound of claim 9 wherein:

$n_5$ is from 2 to 50, $n_6$ is from 1 to 3, $n_7$ is from 2 to 5; and

ϕ is —($CH_2$—$CH_2$)— and ψ is —($CH_2$—($CH_2$—$CH_2$—O)$_3$—$CH_2$—$CH_2$—$CH_2$)— or —($CH_2$—$CH_2$—$CH_2$—(O—$CH_2$—CH)$_3$—$CH_2$)—.

11. The thioester or selenoester compound of claim 1 wherein Y comprises an N-terminal group that supports chemical ligation.

12. The thioester or selenoester compound of claim 11 wherein the N-terminal group comprises cysteine or selenocysteine.

13. The thioester or selenoester compound of claim 12 wherein the cysteine or selenocysteine is protected.

14. A method of cleaving a thioester or selenoester compound from a solid support, said method comprising:

providing a thioester or selenoester generator having the formula:

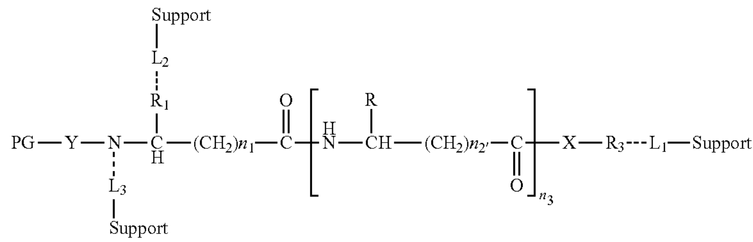

wherein PG is a protecting group that may be present or absent,

Y is an amino acid, a peptide, or a polypeptide and may be present or absent, and when Y is absent PG is an amino protecting group that may be present or absent;

R and $R_1$ are individually selected from the group consisting of: hydrogen, a side chain of an amino acid, a branched alkane, a cycloalkane, an alkyl-substituted aryl or heteroaryl group, and combinations thereof;

$R_3$ is a group compatible with a thioester or selenoester and comprises a water-soluble polymer of a formula selected from the group consisting of: —[C(O)-ϕ-C(O)—NH-ψ-NH]$n_5$ and —[NH-ψ-NH—C(O)-ϕ-C(O)]$n_5$, where $n_5$ is an integer from 2 to 100, and ϕ and ψ are divalent radicals that may be the same or different and are selected from the group consisting of —(($CH_2$)$n_6$-($CH_2CH_2O$)$n_7$-($CH_2$)$n_6$-)- and —(($CH_2$)$n_6$-(O—$CH_2$—$CH_2$)$n_7$-($CH_2$)$n_6$-)-, where $n_6$ is an integer from 1 to 6 and $n_7$ is an integer from 2-50;

X is sulfur or selenium;

$n_1$ and $n_2$ each are from 0 to 2; $n_3$ is from 0 to 100;

each $L_1$, $L_2$ and $L_3$ is a linker cleavable under non-nucleophilic conditions wherein only one of $L_1$, $L_2$, and $L_3$ is present;

Support is a solid phase, matrix or surface; and (b) cleaving said linker under non-nucleophilic conditions to generate a thioester or selenoester compound comprising the formula:

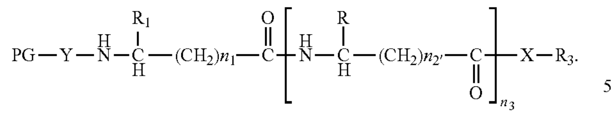

15. A thioester or selenoester generator comprising a composition having the formula:

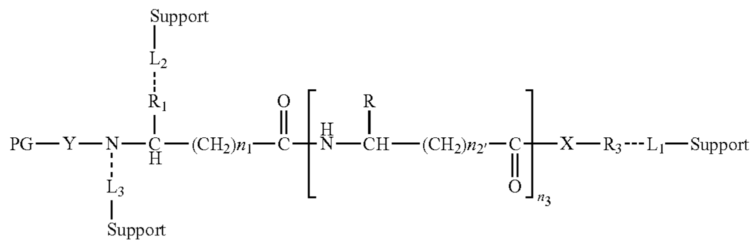

wherein PG is a protecting group that may be present or absent,

Y is an amino acid, a peptide, or a polypeptide and may be present or absent, and when Y is absent PG is an amino protecting group that may be present or absent;

R and $R_1$ are individually selected from the group consisting of: hydrogen, a side chain of an amino acid, a branched alkane, a cycloalkane, an alkyl-substituted aryl or heteroaryl group, and combinations thereof;

$R_3$ is a group compatible with a thioester or selenoester and comprises a water-soluble polymer of a formula selected from the group consisting of: —[C(O)-ϕ-C(O)—NH-ψ-NH]$n_5$ and —[NH-ψ-NH—C(O)-ϕ-C(O)]$n_5$, where $n_5$ is an integer from 2 to 100, and ϕ and ψ are divalent radicals that may be the same or different and are selected from the group consisting of —(($CH_2$)$n_6$-($CH_2CH_2O$)$n_7$-($CH_2$)$n_6$-)- and —(($CH_2$)$n_6$-(O—$CH_2$—$CH_2$)$n_7$-($CH_2$)$n_6$-)-, where $n_6$ is an integer from 1 to 6 and $n_7$ is an integer from 2-50;

X is sulfur or selenium;

$n_1$ and $n_2$ each are from 0 to 2; $n_3$ is from 0 to 100;

each $L_1$, $L_2$ and $L_3$ is a linker cleavable under non-nucleophilic conditions wherein only one of $L_1$, $L_2$, and $L_3$ is present;

Support is a solid phase, matrix or surface.

* * * * *

SEQUENCE LISTING

<160> NUMBER OF SEQ ID NOS: 4

<210> SEQ ID NO 1
<211> LENGTH: 56
<212> TYPE: PRT
<213> ORGANISM: Artificial Sequence
<220> FEATURE:
<223> OTHER INFORMATION: GRFN-1712 peptide
<220> FEATURE:
<221> NAME/KEY: VARIANT
<222> LOCATION: (1)...(1)
<223> OTHER INFORMATION: Cys is Acm protected
<220> FEATURE:
<221> NAME/KEY: VARIANT
<222> LOCATION: (56)...(56)
<223> OTHER INFORMATION: Trp is bound to a thioester moiety

<400> SEQUENCE: 1

Cys Ser Leu Asn Glu Lys Ile Thr Val Pro Asp Thr Lys Val Asn Phe
1               5                   10                  15

Tyr Ala Trp Lys Arg Met Glu Val Gly Gln Gln Ala Val Glu Val Trp
            20                  25                  30

Gln Gly Leu Ala Leu Leu Ser Glu Ala Val Leu Arg Gly Gln Ala Leu
        35                  40                  45

Leu Val Lys Ser Ser Gln Pro Trp
    50                  55

<210> SEQ ID NO 2
<211> LENGTH: 56
<212> TYPE: PRT
<213> ORGANISM: Artificial Sequence
<220> FEATURE:
<223> OTHER INFORMATION: GRFN 1712-PLP3 peptide
<220> FEATURE:
<221> NAME/KEY: VARIANT
<222> LOCATION: (1)...(1)
<223> OTHER INFORMATION: Cys is Acm protected
<220> FEATURE:
<221> NAME/KEY: VARIANT
<222> LOCATION: (56)...(56)
<223> OTHER INFORMATION: Trp is bound to a thioester-PLP3-L moiety

<400> SEQUENCE: 2

Cys Ser Leu Asn Glu Lys Ile Thr Val Pro Asp Thr Lys Val Asn Phe
1               5                   10                  15

Tyr Ala Trp Lys Arg Met Glu Val Gly Gln Gln Ala Val Glu Val Trp
            20                  25                  30

Gln Gly Leu Ala Leu Leu Ser Glu Ala Val Leu Arg Gly Gln Ala Leu
        35                  40                  45

-continued

```
Leu Val Lys Ser Ser Gln Pro Trp
    50                  55


<210> SEQ ID NO 3
<211> LENGTH: 51
<212> TYPE: PRT
<213> ORGANISM: Artificial Sequence
<220> FEATURE:
<223> OTHER INFORMATION: GRFN 1852 peptide
<220> FEATURE:
<221> NAME/KEY: VARIANT
<222> LOCATION: (1)...(1)
<223> OTHER INFORMATION: Cys is Acm protected
<220> FEATURE:
<221> NAME/KEY: VARIANT
<222> LOCATION: (51)...(51)
<223> OTHER INFORMATION: Leu is bound to a thioester moiety

<400> SEQUENCE: 3

Cys Leu Ser Gln Leu His Ser Gly Leu Phe Leu Tyr Gln Gly Leu Leu
 1               5                  10                  15

Gln Ala Leu Glu Gly Ile Ser Pro Glu Leu Gly Pro Thr Leu Asp Thr
            20                  25                  30

Leu Gln Leu Asp Val Ala Asp Phe Ala Thr Thr Ile Trp Gln Gln Met
        35                  40                  45

Glu Glu Leu
    50


<210> SEQ ID NO 4
<211> LENGTH: 51
<212> TYPE: PRT
<213> ORGANISM: Artificial Sequence
<220> FEATURE:
<223> OTHER INFORMATION: GRFN 1852-PLP3 peptide
<220> FEATURE:
<221> NAME/KEY: VARIANT
<222> LOCATION: (1)...(1)
<223> OTHER INFORMATION: Cys is Acm protected
<220> FEATURE:
<221> NAME/KEY: VARIANT
<222> LOCATION: (51)...(51)
<223> OTHER INFORMATION: Leu is bound to a thioester-PLP3-Leu moiety

<400> SEQUENCE: 4

Cys Leu Ser Gln Leu His Ser Gly Leu Phe Leu Tyr Gln Gly Leu Leu
 1               5                  10                  15

Gln Ala Leu Glu Gly Ile Ser Pro Glu Leu Gly Pro Thr Leu Asp Thr
            20                  25                  30

Leu Gln Leu Asp Val Ala Asp Phe Ala Thr Thr Ile Trp Gln Gln Met
        35                  40                  45

Glu Glu Leu
    50
```